United States Patent
Serre et al.

(10) Patent No.: US 8,940,392 B2
(45) Date of Patent: Jan. 27, 2015

(54) TITANIUM BASED INORGANIC-ORGANIC HYBRID SOLID MATERIAL, METHOD FOR PREPARING SAME AND USES THEREOF

(75) Inventors: Christian Serre, Plaisir (FR); Gérard Ferey, Paris (FR); Clément Sanchez, Bures sur Yvette (FR); Laurence Rozes, Brunoy (FR); Meenakshi Dan, Cleveland, OH (US); Théo Frot, Paris (FR)

(73) Assignee: Universite Pierre et Marie Curie (Paris 6), Paris (FR)

( * ) Notice: Subject to any disclaimer, the term of this patent is extended or adjusted under 35 U.S.C. 154(b) by 582 days.

(21) Appl. No.: 13/146,720

(22) PCT Filed: Feb. 18, 2010

(86) PCT No.: PCT/FR2010/050271
§ 371 (c)(1),
(2), (4) Date: Jan. 17, 2012

(87) PCT Pub. No.: WO2010/094889
PCT Pub. Date: Aug. 26, 2010

(65) Prior Publication Data
US 2012/0121904 A1     May 17, 2012

(30) Foreign Application Priority Data
Feb. 18, 2009   (FR) .................................... 09 00744

(51) Int. Cl.
*B32B 5/16*     (2006.01)

(52) U.S. Cl.
USPC ............ 428/402; 428/34.4; 556/51; 502/102; 502/150; 502/300

(58) Field of Classification Search
USPC .............. 428/34.4, 402; 556/44, 51; 502/167, 502/102, 150, 300
See application file for complete search history.

(56) References Cited

U.S. PATENT DOCUMENTS

| | | | |
|---|---|---|---|
| 6,929,679 B2 | 8/2005 | Muller et al. | |
| 7,279,517 B2 | 10/2007 | Mueller et al. | |
| 7,855,299 B2 * | 12/2010 | Jhung et al. | ..................... 556/44 |
| 8,173,827 B2 * | 5/2012 | Chang et al. | .................... 556/44 |
| 8,569,193 B2 * | 10/2013 | Chang et al. | ................. 502/104 |

FOREIGN PATENT DOCUMENTS

| | | | |
|---|---|---|---|
| WO | 2007118888 | | 10/2007 |
| WO | 2008082087 | | 7/2008 |
| WO | WO2008/082087 | * | 7/2008 |

OTHER PUBLICATIONS

International Search Report dated Jun. 17, 2010.

* cited by examiner

*Primary Examiner* — Leszek Kiliman
(74) *Attorney, Agent, or Firm* — Sofer & Haroun, LLP

(57) ABSTRACT

The invention relates to a titanium based polycarboxylate inorganic-organic hybrid solid material that has a pseudo-cubic crystalline structure, to a method for preparing the same using a solvo-thermal procedure, and to the uses thereof in particular for the storage of gases, the adsorption of liquids, the separation of liquids or gases, and the applications thereof in optics or catalysis, in the biomedical (controlled release drug), cosmetic fields, etc.

20 Claims, 9 Drawing Sheets a  b a                                        b

TITANIUM BASED INORGANIC-ORGANIC HYBRID SOLID MATERIAL, METHOD FOR PREPARING SAME AND USES THEREOF

RELATED APPLICATIONS

This application is a National Phase application of PCT/FR2010/050271, filed on Feb. 18, 2010, which in turn claims the benefit of priority from French Patent Application No, 09 00744, filed on Feb. 18, 2009, the entirety of which is incorporated herein by reference.

BACKGROUND

1. Field of the Invention

The present invention relates to a material that is in the form of hybrid crystalline three-dimensional lattices, in particular based on titanium, to the process of preparing same and also to the use thereof, especially for the storage of gases such as $H_2$, $CO_2$ or $CH_4$, the adsorption of liquids, the separation of liquids or gases, applications in optics or in catalysis, in the biomedical field (controlled release of medicaments), cosmetic field, etc.

2. Description of Related Art

Metallo-organic lattices or metal-organic frameworks (MOFs) are coordination polymers, having an inorganic-organic hybrid framework that comprise metal ions and organic ligands coordinated to the metal ions. These materials are organized into one-, two- or three-dimensional lattices, in which the metallic species are joined together periodically by spacer ligands. The framework of these solids has both inorganic parts and organic parts, the cavities of which may be occupied by water molecules or by organic molecules that are easy to extract without deterioration of the backbone. This nevertheless results in a thermal stability lower than that of conventional inorganic porous solids (typically 300° C.); in compensation, the density of the hybrid phases is greatly reduced, typically between 0.2 and 1 g·cm$^{-3}$, with, as a result, (BET) specific surface areas of up to 4500 m$^2$·g$^{-1}$, and pore volumes (<2 cm$^{-3}$·g$^{-1}$) that are considerably increased.

Another distinctive feature of certain hybrid solids is the existence of a flexibility of the lattice, greater than that encountered for purely inorganic phases. This is generally due to the use of flexible organic ligands (aliphatic chains), or to the shrinkage of the pores linked to the departure of molecules encapsulated within the pores.

These materials have a crystalline structure, are usually porous and offer many potential industrial applications such as gas storage, adsorption of liquids, separation of liquids or gases, catalysis, controlled release of medicaments, etc. Mention may be made, for example, of U.S. Pat. No. 7,279,517 which describes a reaction process involving a catalysis system comprising a zinc-based MOF material. This same material is also used for gas storage in U.S. Pat. No. 6,929,679.

Although MOFs exist with almost all the elements of the Periodic Table, from alkaline-earth elements (Ca, Mg) to transition metals (Sc, Fe, V, Cr, Co, Ni, Zn), 3p elements (Al, Ga, In) to rare earths (La, Ce, Eu . . . Y) and actinides (U), the number of porous MOFs based on titanium is still very limited.

Among all of the titanium-based MOFs synthesized to date, mention may especially be made of several types of open-framework titanium diphosphonates.

Among such disphosphonates, only an MOF of titanium obtained hydrotherrnally from $TiO_2$ and from di-N,N'-piperazinebismethylenephosphinic acid (MIL-91(Ti): Serre C. et al., Chem. Mater., 2006, 18, 1451-1457) has a nitrogen-accessible porosity with a (BET) specific surface area close to 300 m$^2$·g$^{-1}$ and a pore size of the order of 4 Å. MOFs based on 1,4-butanediol or on phthalocyanine have also been identified recently without the latter having a significant specific surface area or porosity.

Although the first zirconium (IV) polycarboxylates were described recently, in particular in the article by J. Hafizovic Cavka et al., J.A.C.S., 2008, 130, 13850-13851, there is not, to date, any crystallized titanium (IV) polycarboxylate described in the literature.

International application WO2007/118888 refers to the synthesis of carboxylate MOFs based on titanium or on zirconium via a solvothermal route using a precursor of titanium such as, for example, $TiOSO_4$, $H_2O$ and terephthalic acid in pure DMF, at a temperature of 130° C. for 18 hours. This process does not however make it possible to attain titanium-based polycarboxylate MOFs having a crystalline structure and a porosity that are satisfactory.

OBJECTS AND SUMMARY

However, the presence of titanium atoms within porous solid materials is advantageous in so far as it may give the MOF materials incorporating them advantageous redox properties in optics or in catalysis.

For example, photochromic MOFs could be obtained by reaction of a titanium MOF with light. Indeed, under the action of light irradiation, the Ti$^{4+}$ species are reduced to Ti$^{3+}$. The presence of these reduced species leads to the formation of a compound having a mixed valency that exhibits a characteristic coloration.

Furthermore, due to its recognized non-toxicity (DL$_{50}$>12 g/kg), titanium may be used in cosmetics or in biology.

It would therefore be advantageous to be able to have titanium-based MOFs having a high specific surface area for applications in the field of gas storage/separation, catalysis, or even biological or cosmetic applications.

The objective of the present invention is therefore to provide titanium MOFs having a high specific surface area (nitrogen-accessible porosity), and also a simple reliable and inexpensive synthesis process that makes it possible to attain this type of material.

One subject of the present invention is an inorganic-organic hybrid solid-material based on titanium, characterized in that it has a pseudo-cubic crystalline structure and that it is constituted exclusively of units of formula (I) below:

$$\text{Ti}_a\text{O}_b(\text{OH})_c[(^-\text{OOC})-\text{X-\#}]_d \qquad (I)$$

in which:
X is an organic spacer and represents a saturated or unsaturated, linear or branched, aliphatic chain having 2 to 12 carbon atoms; a monocyclic, bicyclic or tricyclic hydrocarbon-based aromatic group that is unsubstituted or that is substituted by one or more substituents R independently chosen from a halogen atom and amino, nitro, hydroxyl, $C_1$-$C_4$ trifluoroalkyl and $C_1$-$C_4$ alkyl groups: a benzophenone group; a monocyclic or bicyclic heteroaromatic group in which the ring(s) is(are) 5- or 6-membered ring(s), said group containing at least one heteroatom chosen from nitrogen and sulfur and being unsubstituted or substituted by one or more substituents R independently chosen from a halogen atom and amino, nitro, hydroxyl, $C_1$-$C_4$ trifluoroalkyl and $C_1$-$C_4$ alkyl groups;
a and b, which are identical or different, are integers varying from 1 to 16 inclusively;

c and d, which are identical or different, are integers varying from 1 to 32 inclusively;

the indices a, b, c and d adhere to the relation 4a=2b+c+d;

the titanium atoms form a purely inorganic elementary building block constituted of titanium oxo complexes;

# is the point through which two units of formula (I) are joined together; # represents a covalent bond between a carbon atom belonging to the spacer X and the carbon atom of a carboxylate group $COO^-$ of another unit of formula (I) and in which the two oxygen atoms of the carboxylate group belong respectively to two adjacent octahedral titanium oxo complexes of an elementary building block of said other unit of formula (I);

said units of formula (I) together forming a three-dimensional structure and defining cavities having a free diameter of approximately (pores or cages) 4 to 40 Å that are accessible through triangular apertures having dimensions of approximately 4 to 15 Å.

According to the invention, the expression "three-dimensional structure" is understood to mean a three-dimensional sequence or repetition of units of formula (I) as is conventionally understood in the field of MOF materials, that are also characterized as "organometallic polymers".

The solid material in accordance with the invention, referred to hereinbelow as titanium MOF, has the advantage of being based on titanium and of having a controlled and highly organized crystalline structure, with a particular topology and a particular distribution that gives this material specific properties.

The crystalline spatial organization of the solid material of the present invention is the basis of the particular characteristics and properties of this material, and especially governs the size of the cavities (or pores) which has an influence on the specific surface area of the material and on the capacities for storing gases or for adsorbing liquids for example. The size of the pores may thus be adjusted by the choice of the organic spacer X.

Among the aliphatic chains defined for X, mention may be made of linear alkyl chains such as ethyl, propyl, butyl, pentyl, hexyl, heptyl, octyl, nonyl, decyl, undecyl and dodecyl chains; linear alkene chains such as ethylene, propylene, butylene, pentylene, hexylene, heptylene, octylene, nonylene, decylene, undecylene and dodecylene; alkyne chains such as ethyne, propyne, butyne, pentyne, hexyne, heptyne, octyne, nonyne, decyne, undecyne and dodecyne. Among such chains, $C_1$-$C_4$ alkyl chains and $C_2$-$C_4$ alkene or alkyne chains are preferred.

Among the hydrocarbon-based aromatic groups defined for X, mention may especially be made of phenylene; chlorophenylene; bromophenylene; aminophenylene; nitrophenylene; mono-, di- or tetramethylphenylene; mono- or diethenylphenylene; mono- or dihydroxyphenylene; biphenylene; diphenyldiazene; naphthalene and anthracene groups.

Among the heterocycles defined for X, mention may be made of thiophene, bithiophene, pyridine, bipyridine and pyrazine rings.

According to one preferred embodiment of the invention, the subunit [$^-$OOC—X-#] is chosen from the groups of formulae (II-1) to (II-13) below:

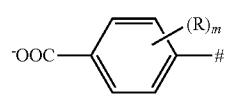
(II-1)

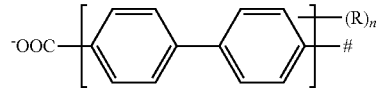
(II-2)

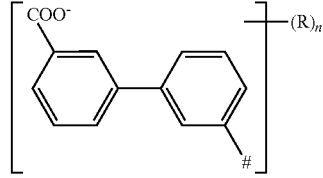
(II-3)

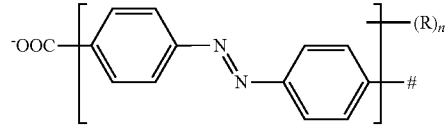
(II-4)

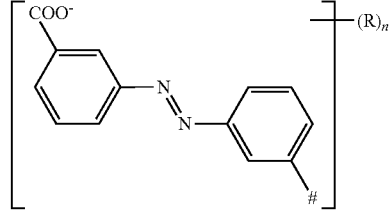
(II-5)

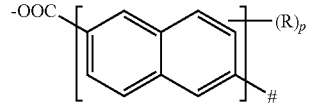
(II-6)

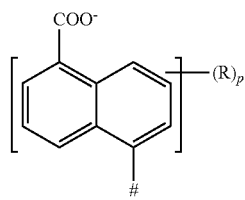
(II-7)

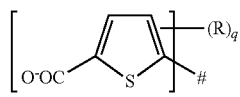
(II-8)

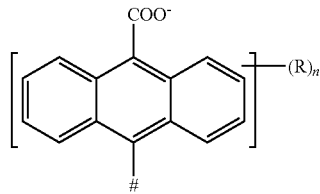
(II-9)

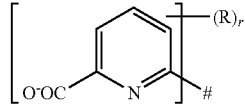
(II-10)

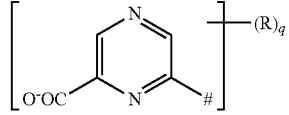
(II-11)

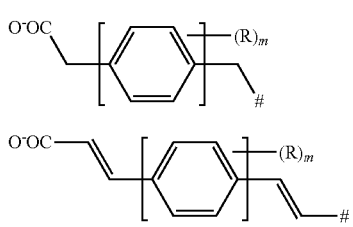

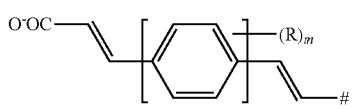

in which:
R is a halogen atom, an amino, nitro, hydroxyl, $C_1$-$C_4$ trifluoroalkyl or $C_1$-$C_4$ alkyl group;
m is an integer ranging from 0 to 4;
n is an integer ranging from 0 to 8;
p is an integer ranging from 0 to 6;
q is an integer ranging from 0 to 2; and
r is an integer ranging from 0 to 3.

Among the subunits of formula (II-1), phenyl-1-carboxylate, phenyl-2-amino-1-carboxylate, phenyl-2,5-dihydroxy-1-carboxylate and phenyl-2-chloro-1-carboxylate are particularly preferred.

Among the subunits of formula (II-4), mention may especially be made of azobenzene-4-carboxylate, azobenzene-3,3'-dichloro-4-carboxylate and azobenzene-3,3'-dihydroxy-4-carboxylate.

Among the subunits of formula (II-8), mention may be made of thiophene-2-carboxylate and 3,4-dihydroxythiophene-2-carboxylate.

According to one particularly preferred embodiment of the invention, the subunit [$^-$OOC—X-#] is chosen from phenyl-1-carboxylate, phenyl-2-amino-1-carboxylate, and thiophene-2-carboxylate.

Among the subunits of formula (I) as defined previously, mention may very particularly be made of the subunits of formula (I-1) below:

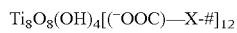

in which:
X and # are as defined previously;
the titanium atoms form a purely inorganic elementary building block constituted of 8 octahedral titanium oxo complexes each comprising a central titanium atom surrounded by 6 oxygen atoms, said octahedral titanium oxo complexes being joined together either by a common edge, or by a common apex, in both cases by means of oxo-O— or hydroxo-OH— bridges; said building blocks being connected together in the three dimensions of space by organic spacers X; it being understood that each of the building blocks is connected to 12 organic spacers by means of carboxylate groups COO$^-$ in which each of the two oxygen atoms is an integral part of two adjacent titanium oxo complexes.

In the subunits of formula (I-1), an elementary building block (or wheel of octahedral titanium oxo complexes) therefore contains 36 oxygen atoms connected to eight titanium atoms alternately either via a common edge involving two oxo or hydroxo bridges or by a common apex involving a single oxo or hydroxo bridge, or by means of carboxylate groups.

As has been seen previously, the solid material in accordance with the present invention comprises cavities having a free diameter of 4 to 40 Å approximately. Preferably, the cavities have a free diameter of 5 to 12.6 Å approximately.

The solid material in accordance with the invention has a (BET) specific surface area of 200 to 6000 m$^2$/g approximately, preferably from 200 to 1800 m$^2$/g.

Within the context of the invention, the pore volume means the volume of gas accessible for the gas and/or liquid molecules and corresponds to the volume inside what are referred to either as "cavities", "cages" or "pores" in the text of the present application.

The solid material in accordance with the invention may have a pore volume of 0.1 to 3 cm$^3$/g approximately, more particularly of 0.5 to 0.7 cm$^3$/g approximately.

Owing to these properties, the solid material in accordance with the present invention may be used as a catalyst support for carrying out heterogeneous catalyzed chemical reactions or as a gas storage/separation material or as a matrix for encapsulating active principles (medicaments, cosmetics) or else as a photochromic material for information storage, laser printing or else as an oxygen indicator material.

As nonlimiting examples, the solid material in accordance with the present invention more particularly being used:
for the adsorption of greenhouse gases ($CO_2$, $CH_4$), in the presence of various contaminants (water, $N_2$, CO, $H_2S$, etc.) in processes for capturing flue gases from factories (steelworks, cement works, thermal power plants, etc.), from units for producing methane or hydrogen from the combustion of biomass or the gasification of coal. The low production cost of these materials, combined with their non-toxicity and their good stability (thermal stability, moisture resistance or resistance to dihydrogen sulfide) makes them the candidates of choice for large-scale applications of this type;
for the separation of fluids (gases, vapors, liquids) such as the separation of aromatic compounds (isomers of xylene), of branched alkanes (octane number), the purification of fuels, etc.;
in biology/cosmetics, for the adsorption or encapsulation of active (pharmaceutical or cosmetic) principles of interest for the purpose either of releasing them in a controlled manner in order to provide doses at an effective level therapeutically for a suitable period, or of protecting them with respect to the outside environment (from moisture for example). As such, titanium is a metal that is not very toxic (lethal dose ($DL^{50}$) greater than 5 g/kg) in the same way as carboxylic acids in general, which gives these solids (titanium carboxylates) an a priori low toxicity that is very advantageous for this type of application. The UV adsorption properties of titanium may be applied to the field of UV-screening substances used in cosmetics, in particular with a suitable choice of organic spacer that itself also adsorbs in this wavelength range. The solid materials in accordance with the invention may also be used for the encapsulation of toxins, for detoxification (for eliminating a posteriori toxins in the body), or for purifying biological fluids (urine, blood, etc.).

The solid material in accordance with the invention may be prepared under solvothermal conditions in a mixture of at least two solvents, either directly starting from titanium precursors of titanium alkoxide type and from at least one dicarboxylic acid, or indirectly starting from preformed species such as oxo complexes of titanium and of at least one dicarboxylic acid.

Thus, another subject of the present invention is a process for preparing an inorganic-organic hybrid solid material based on titanium as defined previously, characterized in that it comprises the following steps:

1) in a first step, a reaction mixture is prepared comprising:
i) at least one titanium precursor chosen from titanium alkoxides of formula (III) below:

$$Ti(OR_1)_4 \quad (III)$$

in which $R_1$ is a linear or branched alkyl radical comprising from 1 to 4 carbon atoms or at least one titanium oxo complex of formula (IV) below:

$$Ti_xO_y(OR_2)_z(OOCR_3)_w \quad (IV)$$

in which:
$R_2$ represents a hydrogen atom, a linear or branched $C_1$-$C_6$ alkyl radical or a phenyl ring optionally substituted by one or more radicals chosen from a halogen atom, $C_1$-$C_4$ alkyl and $C_2$-$C_3$ alkene radicals;
$R_3$ represents a linear or branched $C_1$-$C_4$ alkyl radical, a $C_1$-$C_4$ trihaloalkyl radical or a phenyl ring;
x is an integer ranging from 2 to 18;
y is an integer ranging from 1 to 27;
z is an integer ranging from 0 to 32;
w is an integer ranging from 0 to 16;
and in which the titanium atoms form an elementary building block constituted of a purely inorganic core of titanium oxo complexes in octahedral coordination each comprising a central titanium atom surrounded by 6 oxygen atoms, said octahedral titanium oxo complexes being joined together either by a common edge, or by a common apex, in both cases by means of oxo-O— or hydroxo-OH— bridges; said building blocks being surrounded by organic ligands of alcoholate ($OR_2$) and/or carboxylate ($OOCR_3$) type;
ii) at least one dicarboxylic acid of formula (V) below:

$$HOOC—X'—COOH \quad (V)$$

in which X' represents a saturated or unsaturated, linear or branched, aliphatic chain having from 2 to 12 carbon atoms, a benzophenone group or a monocyclic, bicyclic or tricyclic hydrocarbon-based aromatic group that is unsubstituted or that is substituted by one or more substituents R' independently chosen from a halogen atom and amino, nitro, hydroxyl, $C_1$-$C_4$ trifluoroalkyl and $C_1$-$C_4$ alkyl groups;
iii) a mixture of at least two organic solvents comprising at least one solvent S1 chosen from $C_1$-$C_4$ alcohols, benzyl alcohol and chlorobenzyl alcohol, and at least one solvent S2 chosen from N,N-dimethylformamide (DMF), N,N-diethylformamide (DEF), dimethylsulfoxide (DMSO), ethylene glycol, dioxane, acetonitrile, acetone, tetrahydrofuran (THF), pyridine and N-methylpyrrolidone;
2) in a second step, the reaction mixture thus obtained is brought to a temperature of 70 to 200° C. approximately, for approximately 4 to 72 hours, until a precipitate corresponding to the expected solid material is obtained; then
3) in a third step, the reaction mixture is cooled to ambient temperature;
4) in a fourth step, the solid material is separated from the mixture of organic solvents;
it being understood that when the solid material is constituted of units of formula (I) in which X is a monocyclic or bicyclic heteroaromatic group in which the ring(s) is(are) optionally substituted 5- or 6-membered ring(s), said group containing at least one heteroatom chosen from nitrogen and sulfur, then said process also comprises the following additional steps:

5) a fifth step of preparing a dispersion of the solid material resulting from the fourth step in at least one polar organic solvent, in the presence of at least one dicarboxylic acid of formula (VI) below:

$$HOOC—X''—COOH \quad (VI)$$

in which X'' represents a monocyclic or bicyclic heteroaromatic group in which the ring(s) is(are) 5- or 6-membered ring(s), said group containing at least one heteroatom chosen from nitrogen and sulfur and being unsubstituted or substituted by one or more substituents R independently chosen from a halogen atom and amino, nitro, hydroxyl, $C_1$-$C_4$ trifluoroalkyl and $C_1$-$C_4$ alkyl groups;
6) a sixth step, during which the dispersion thus obtained is brought to a temperature of 100 to 150° C. for a time of 4 hours to 4 days, which leads to the formation of a precipitate corresponding to the expected solid material; then
7) a seventh step during which the temperature is allowed to return to ambient temperature; and
8) an eighth step of separating the solid material thus obtained from the organic solvent(s).

According to one preferred embodiment of this process, the precursors of formula (III) are chosen from titanium ethoxide, titanium isopropoxide, titanium n-propoxide and titanium butoxide. Among such precursors, titanium isopropoxide is particularly preferred.

The titanium oxo complexes of formula (IV) that can be used according to the process of the invention are, for example, described in the article by Rozes L. et al., Monatshefte für Chemie, 2006, 137, 501-528. Among the titanium oxo complexes of formula (IV), above, mention may especially be made of $Ti_{16}O_{16}(OCH_2CH_3)_{32}$ and $Ti_8O_8(OOCR_3)_{16}$ in which $R_3$ is as defined previously (a $C_1$-$C_4$ linear or branched alkyl radical, a $C_1$-$C_4$ trihaloalkyl radical or a phenyl ring).

The dicarboxylic acids of formula (V) are obviously chosen from the dicarboxylic acids corresponding to the subunits [⁻OOC—X-#] of the solid material that it is desired to prepare, within the limit however of the definition given for X' above. Indeed, it is not a priori possible to directly, through the first step, attain materials in which X is a 5- or 6-membered heterocycle. In this case, the process in accordance with the invention must comprise steps 5 to 8 during which spacers X' are exchanged for spacers X" as defined above.

The dicarboxylic acid of formula (V) may thus, in particular, be chosen from benzene-1,4-dicarboxylic acid (terephthalic acid), 2-aminobenzene-1,4-dicarboxylic acid (aminoterephthalic acid), 2-nitrobenzene-1,4-dicarboxylic acid, 2-chlorobenzene-1,4-dicarboxylic acid, 2-bromobenzene-1,4-dicarboxylic acid, 2,5-dihydroxybenzene-1,4-dicarboxylic acid, 2-methylbenzene-1,4-dicarboxylic acid, 2,5-dimethylbenzene-1,4-dicarboxylic acid, diphenyl-4,4'-dicarboxylic acid, diphenyl-3,3'-dicarboxylic acid, 4,4'-(diazene-1,2-diyl) dibenzoic acid, 3,3'-(diazene-1,2-diyl)dibenzoic acid, naphthalene-2,6-dicarboxylic acid, naphthalene-1,5-dicarboxylic acid, 1,4-phenylenediacetic acid, 1,4-phenylenediacrylic acid and 4,4'-benzophenonedicarboxylic acid.

Among such acids, benzene-1,4-dicarboxylic acid, 2,5-dihydroxybenzene-1,4-dicarboxylic acid and 2-aminobenzene-1,4-dicarboxylic acid are particularly preferred.

Within the reaction mixture, the titanium alkoxide of formula (III) or titanium oxo complex of formula (IV)/dicarboxylic acid of formula (V) molar ratio preferably varies from 0.1 to 2 approximately and more preferably still from 0.5 to 1 approximately.

Among the $C_1$-$C_4$ alcohols (S1) used during the first step of the process, methanol is particularly preferred.

Within the mixture of organic solvents used during the first step of the process, the S1/S2 volume ratio preferably varies from 0.05 to 0.95 approximately, and more preferably still from 0.10 to 0.90 approximately.

Optionally, the reaction mixture used during the first step may also contain one or more additives chosen from monocarboxylic acids such as, for example, acetic acid and organic bases such as, for example, alkylamines for instance triethylamine. The inventors have in particular observed that the presence of a monocarboxylic acid such as acetic acid makes it possible to improve the crystallinity of the solid material in accordance with the invention and/or the yield of the reaction. The presence of such additives may also make it possible to decrease the duration of the synthesis.

When they are used, these additives preferably represent from 1 to 10% by weight and more preferably still from 1 to 5% by weight relative to the total weight of the reaction mixture.

According to one preferred embodiment, the second step of the process is carried out at a temperature of 100 to 150° C. approximately.

The duration of the second step will vary as a function of the temperature used, it being understood that the higher the temperature, the shorter this duration is. Preferably, the duration of the second step varies from 8 to 15 hours approximately.

According to one particular embodiment of the process in accordance with the invention, step 2) is carried out using a microwave oven. In this case, the duration of the second step may be reduced and may vary from 1 minute to 60 minutes. This method of heating the reaction mixture furthermore makes it possible to attain materials having a particle size much smaller than that of the particles of material obtained when heating is carried out in a conventional oven, During the third step, the cooling of the reaction mixture to ambient temperature is preferably carried out at a cooling rate of 1° C./hour to 40° C./hour approximately.

The polar solvents that can be used during the fifth step may especially be chosen from mixtures of at least two organic solvents S1 and S2 comprising at least one solvent S1 chosen from $C_1$-$C_4$ alcohols, benzyl alcohol and chlorobenzyl alcohol, and at least one solvent S2 chosen from N,N-dimethylformamide (DMF), N,N-diethylformamide (DEF), dimethylsulfoxide (DMSO), ethylene glycol, dioxane, acetonitrile, acetone, tetrahydrofuran (THF), pyridine and N-methylpyrrolidone.

As has been seen previously, when the solid material in accordance with the present invention is constituted of units of formula (I) in which X is a 5- or 6-membered aromatic heterocycle containing at least one heteroatom chosen from nitrogen and sulfur, it is essential to carry out steps 5) to 8) as defined above, during which the spacer X' is exchanged with a spacer X" as defined previously.

During the fifth step, the solid material resulting from the fourth step is obtained with a yield of 50 to 75% approximately.

Among the dicarboxylic acids of formula (VI), mention may in particular be made of thiophene-2,5-dicarboxylic acid, pyridine-2,5-dicarboxylic acid, pyrazine-2,5-dicarboxylic acid, pyridine-2,6-dicarboxylic acid, pyrazyne-2,3-dicarboxylic acid and pyrazine-2,6-dicarboxylic acid. Among these acids, thiophene-2,5-dicarboxylic acid is particularly preferred.

The solid material resulting from the fourth step/dicarboxylic acid of formula (VI) molar ratio during the fifth step varies preferably from 1 to 20 approximately and more preferably still from 5 to 10 approximately.

According to one preferred embodiment of the process of the invention, the sixth step is carried out over a duration of 8 to 15 hours approximately.

The fourth and eighth steps of separating the solid material from the mixture of organic solvents may be carried out by any separation method known to a person skilled in the art, among which filtration is preferred.

When the synthesis is complete, the solid material is preferably washed, either very rapidly statically, or by redispersion in a solvent at ambient temperature with stirring, for example with an organic solvent such as for example DMF, then dried by any appropriate drying technique known to a person skilled in the art. This drying step makes it possible to eliminate any trace of solvent and/or of acid. It may especially be carried out by calcination of the solid material in air or under vacuum, at a temperature of 100 to 275° C. for a duration of 3 to 48 hours, preferably of 10 to 15 hours.

The present invention is illustrated by the following exemplary embodiments, to which it is not however limited.

DETAILED DESCRIPTION

Examples

Figure 1:
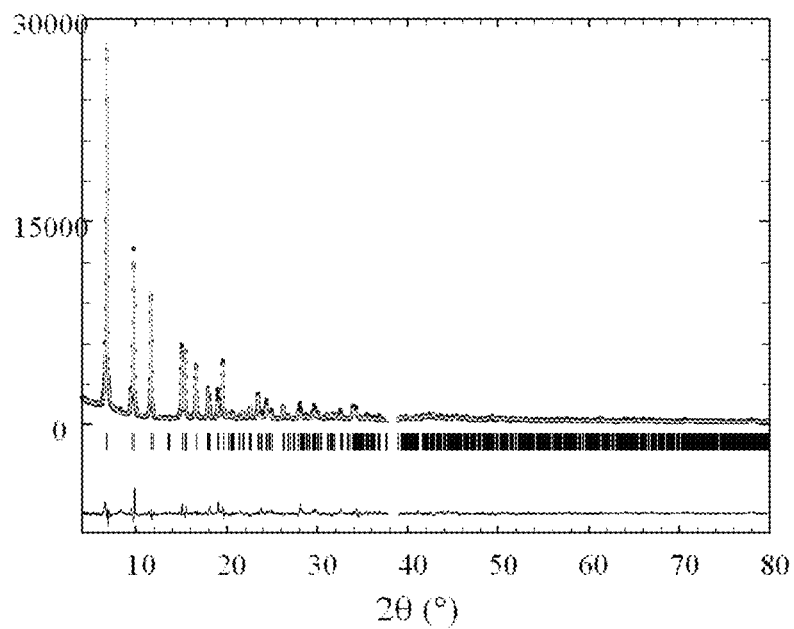
FIG. 1 is a XRD diffraction diagram as per example 1 in accordance with one embodiment.

In the following examples, the structures of the materials obtained were determined from their X-ray powder diffractogram (XRD diffractogram according to the Rietveld method) on a Bruker D5000 machine.

The crystallographic lattices were obtained using Dicvol software (A. Boultif, et al. J. Appl. Crystallogr., 1991, 24, 987) and the refinement by lattice strains was carried out by virtue of the Fullprof software (Rodriguez-Carvajal, J. in "Collected Abstracts of Powder Diffraction Meeting", Toulouse, France 1990, 127) and its graphical interface Win-PLOTR (Roisnel, T. et al., In "Abstracts of the 7$^{th}$ European Powder Diffraction Conference", Barcelona, Spain 2000, 71). The atomic position of most of the atoms constituting the structures of the materials obtained was determined by a direct method by virtue of the Expo program (Altomare, A et al., J. Appl. Ciystallogr., 1999, 32, 339). The position of the residual atoms and also of the free water molecules was determined by virtue of the SHELXL-97 program (University of Gottingen, Germany, 1997). The atomic positions were then refined in Fullprof still using the WinPLOTR graphical interface. Strains of distances and of angles between the atoms (distances: Ti—O, C—C and C—O; angles O—Ti—O and O—C—O, C—C—C) were applied during the refinement.

Thermogravimetric analyses were carried out using a thermogravimetric analyzer sold under the reference TA 2050 by TA Instruments or an STA6000 analyzer from Perkin Elmer, under a stream of air (80 cm$^{-3}$·min$^{-1}$) with a heating rate of 3° C./minute and using around 5 mg of material.

Infrared spectroscopy analyses were carried out on a spectrometer sold under the name Nicolet 750, using KBr pellets containing the material to be analyzed in trace amounts.

The specific surface area measurements were carried out by nitrogen adsorption-desorption techniques using a machine sold under the name Micromeritics ASAP 2010, on around 50 mg of material previously activated under a primary vacuum (10$^{-3}$ Torr) for 15 hours at 200° C., the analysis being carried out by Langmuir or BET calculation methods.

The thermal stability was evaluated using a Bruker D5000 diffractometer equipped with an Anton Paar high-temperature chamber.

Example 1

Synthesis of the TiBDC Phase of Composition Ti$_8$O$_8$(OH)$_4$[O$_2$C—C$_6$H$_4$—CO$_2$]$_6$ 1.5 mmol of 1,4-benzenedicarboxylic acid (250 mg) (Aldrich, 98%) then 1 mmol of titanium isopropoxide Ti(OiPr)$_4$ (0.3 ml) (Acros Organics, 98%), were introduced into a Teflon® body containing 5 ml of a mixture constituted of 4.5 ml of anhydrous dimethylformamide (Acros Organics) and 0.5 ml of methanol (Aldrich, 99.9%). The reaction mixture was stirred for 5 minutes at ambient temperature.

The Teflon® body was then introduced into a PAAR metallic body then put into an oven at 150° C. for 15 hours. After returning to ambient temperature, the expected material in the form of a solid was recovered by filtration, washed with acetone twice and dried in air. The solvent contained in the pores was removed by calcination of the solid at 200° C. in air for 12 hours.

The crystallographic data and structural refinement parameters of the material obtained are given in table 1 below:

TABLE 1

| | |
|---|---|
| Empirical formula (dry phase, with no free water) | Ti$_{16}$O$_{72}$C$_{96}$H$_{64}$ |
| Molar mass (g · mol$^{-1}$) | 3135 |
| Calculated density (g · cm$^{-3}$) (dry phase) | 0.81 |
| Crystalline symmetry | Orthorhombic |
| Space group | I 4/m m m (No. 139) |
| a (Å) | 18.654(1) |
| c (Å) | 18.144(1) |
| V(Å3) | 6313.9(1) |
| Z | 4 |
| Wavelength λ (Cu K$_\alpha$) | 1.54059; 1.54439 |
| χ = K$_{\alpha 2}$/K$_{\alpha 1}$ | 0.5 |
| Temperature (K) | 296 |
| Angular range 2θ (°) | 5-80 |
| Number of reflections (Bragg peaks) | 662 |
| Number of independent atoms | 20 |
| Number of intensity parameters | 37 |
| Number of profile parameters | 10 |
| Number of strains of distances and angles | 35 |
| R$_P$ | 8 |
| R$_{WP}$ | 10.9 |
| R$_{Bragg}$ | 10.4 |
| Overall thermal agitation parameter | 3.9(1) |
| Profile function | Pseudo-Voigt |
| Continuous background | Experimental (32 points) |
| Number of asymmetry parameters | 2 |

The XRD diffraction diagram is represented in the appended FIG. 1, in which the intensity (expressed in arbitrary units) is a function of the diffraction angle in degrees. In this figure, the black points correspond to the experimental points; the grey points correspond to the calculated points; the black lines correspond to the Bragg peaks; and the lowest black curve corresponds to the diagram of difference between the experimental points and the calculated points.

Figure 2:
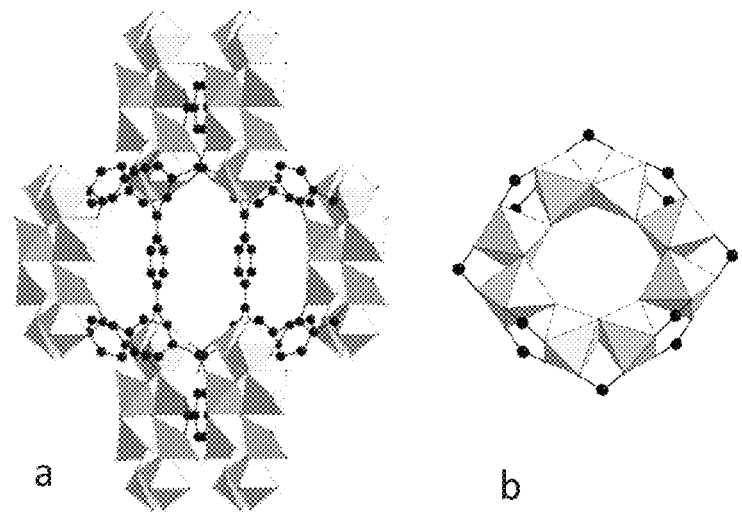
FIGS. 2a and 2b show the crystallographic structure of a material obtained as per example 1 in accordance with one embodiment.

The crystallographic structure of the material obtained is represented schematically in the appended FIG. 2, in which the crystalline structure of the material along the axis a (or b) (FIG. 2a) and also a view of a wheel of titanium octahedra (FIG. 2b, titanium octahedra, carbon atoms: black points) have been represented. The material crystallizes in the orthorhombic space group I 4/mmm (No. 139) with the following parameters:

a=18.654(1) Å, c=18.144(1) Å lattice volume: 6313.9 (6) Å$^3$

This material is constituted of octahedra of titanium TiO$_5$(OH) which assemble into aggregates (or wheels) of eight octahedra connected together by terephthalate anions. The whole assembly defines a pseudo-cubic porous solid with a three-dimensional network of pores. This structure may also be described as an assembly of hybrid "octahedra" with, on each apex of each octahedron, a wheel constituted of eight titanium poiyhedra. The apertures for access to the pores have a free dimension close to 5 to 7 Angströms and two types of cages are present, having dimensions close to 6 and 13 Angströms respectively.

The atomic coordinates of the material obtained are given in table 2 below (hydrated phase):

TABLE 2

| Atom | Wyckoff position | Degree of occupation | x/a | y/b | z/c |
|---|---|---|---|---|---|
| Ti | 16l | | 0.20830 | 0.07400 | 1/2 |
| O1 | 16l | | 0.31110 | 0.05800 | 1/2 |
| O2 | 16n | | 0.18190 | 0 | 0.42650 |
| O3 | 32o | | 0.22590 | 0.14420 | 0.42680 |
| O4 | 8h | | 0.10740 | 0.10740 | 1/2 |
| C1 | 8j | | 0.35070 | 0 | 1/2 |
| C2 | 8j | | 0.42650 | 0 | 1/2 |
| C3 | 16l | | 0.46320 | 0.07050 | 1/2 |
| C4 | 16m | | 0.19400 | 0.19400 | 0.40230 |
| C5 | 16m | | 0.22250 | 0.22250 | 0.32090 |
| C6 | 32o | | 0.20150 | 0.28760 | 0.28980 |
| Ow1 [a] | 8h | | 0.17590 | 0.17590 | 0 |
| Ow2 | 16m | | 0.09180 | 0.09180 | 0.25400 |
| Ow3 | 16n | | 0.40490 | 0 | 0.26520 |
| Ow4 | 4e | | 0 | 0 | 0.56540 |
| Ow5 | 16m | | 0.10650 | 0.10650 | 0.09520 |
| Ow6 | 32o | 50% | 0.24080 | 0.03420 | 0.08380 |
| Ow7 | 16n | 77% | 0.23510 | 0 | 0.22370 |
| Ow8 | 4e | | 0 | 0 | 0.17900 |
| Ow10 | 2a | | | 0 | 0 |

[a] In this table, the water molecules are denoted Owi (i = 1 to 10) and are not, strictly speaking, a part of the structure of the material since they only fill its pores when it is exposed to ambient air.

The main interatomic distances, expressed in Angströms, are given in table 3 below:

TABLE 3

| Ti | O3 | x, y, z | 1.89 (1) |
|---|---|---|---|
| | O3 | x, y, 1 − z | 1.89 (1) |
| | O1 | x, y, z | 1.941 (1) |
| | O2 | x, y, z | 1.98 (1) |
| | O2 | x, −y, 1 − z | 1.98 (1) |
| | O4 | x, y, z | 1.98 (1) |
| Cl | O1 | x, −y, 1 − z | 1.31 (1) |
| | O1 | x, y, z | 1.31 (1) |
| | C2 | x, y, z | 1.41 (1) |
| C2 | C1 | x, y, z | 1.41 (1) |
| | C3 | x, −y, 1 − z | 1.48 (1) |
| | C3 | x, y, z | 1.48 (1) |
| C3 | C3 | 1 − x, y, 1 − z | 1.37 (1) |
| | C2 | x, y, z | 1.48 (1) |
| C4 | O3 | y, x, z | 1.19 (1) |
| | O3 | x, y, z | 1.19 (1) |
| | C5 | x, y, z | 1.65 (1) |
| C5 | C6 | x, y, z | 1.40 (1) |
| | C6 | y, x, z | 1.40 (1) |
| | C4 | x, y, z | 1.65 (1) |
| C6 | C5 | x, y, z | 1.40 (1) |
| | C6 | 0.5 − y, 0.5 − x, 0.5 − z | 1.47 (1) |

Example 2

Synthesis of the Ti—NH$_2$BDC Phase of Ti$_8$O$_8$(OH)$_4$ [O$_2$C—C$_6$H$_3$(NH$_2$)—CO$_2$]$_6$ Composition The Ti—NH$_2$BDC was prepared according to the process indicated above in example 1, using a starting product 1.5 mmol of 2-aminoterephthalic acid (270 mg) (Aldrich, 98%), 0.67 mmol of titanium isopropoxide Ti(OiPr)$_4$ (0.2 ml) (Acros Organics, 98%), and 5 ml of a mixture constituted of 2.5 ml of anhydrous dimethylfomiamide (Acros Organics) and 2.5 ml of methanol (Aldrich, 99.9%).

The Teflon® body was then introduced into a PAAR metallic body then put in an oven at 100° C. for 15 hours. After returning to ambient temperature, the expected material was obtained in the form of a solid, which was recovered by filtration, washed with acetone twice and dried in air. The solvent contained in the pores was removed by calcination of the solid at 200° C. in air for 12 hours.

The crystallographic data and structural refinement parameters of the material obtained are given in table 4 below:

TABLE 4

| Empirical formula (dry phase, with no free water) | Ti$_{16}$O$_{72}$N$_4$C$_{96}$H$_{76}$ |
|---|---|
| Molar mass (g · mol$^{-1}$) | 3315 |
| Calculated density (g · cm$^{-3}$) (dry phase) | 0.86 |
| Crystalline symmetry | Orthorhombic |
| Space group | I 4/m m m (No. 139) |
| a (Å) | 18.673(1) |
| c (Å) | 18.138(1) |
| V (Å3) | 6324.5(1) |
| Z | 4 |
| Wavelength λ (Cu K$_\alpha$) | 1.54059; 1.54439 |
| χ = K$_{\alpha 2}$/K$_{\alpha 1}$ | 0.5 |
| Temperature (K) | 296 |
| Angular range 2θ (°) | 5-80 |
| Number of reflections (Bragg peaks) | 644 |
| Number of independent atoms | 23 |
| Number of intensity parameters | 43 |
| Number of profile parameters | 10 |
| Number of strains of distances and angles | 35 |
| R$_P$ | 11.9 |
| R$_{WP}$ | 15.5 |
| R$_{Bragg}$ | 13.6 |
| Overall thermal agitation parameter | 2.9(1) |
| Profile function | Pseudo-Voigt |
| Continuous background | Experimental (35 points) |
| Number of asymmetry parameters | 2 |

Figure 3:
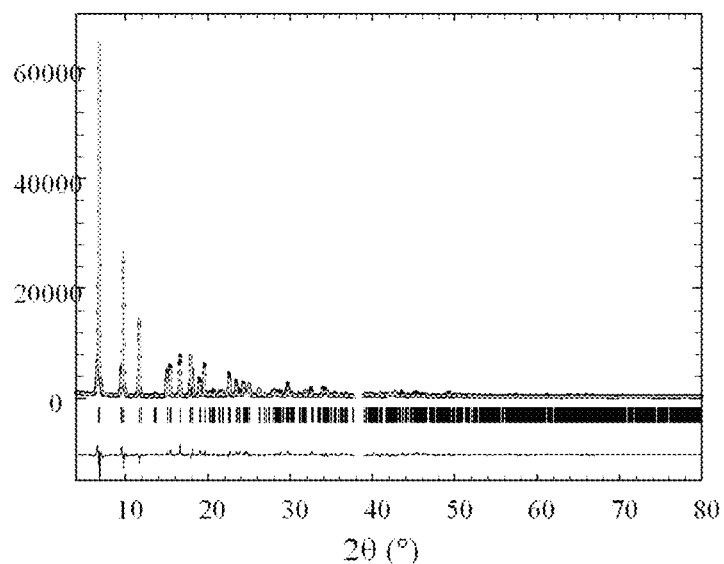
FIG. 3 is a XRD diffraction diagram as per example 2 in accordance with one embodiment.

The XRD diffraction diagram of the material obtained is represented in the appended FIG. 3, in which the intensity (expressed in arbitrary units) is a function of the diffraction angle (in degrees). In this figure, the black points correspond to the experimental points; the grey points correspond to the calculated points; the black lines correspond to the Bragg peaks; and the lowest black curve corresponds to the diagram of difference between the experimental points and the calculated points.

Figure 4:
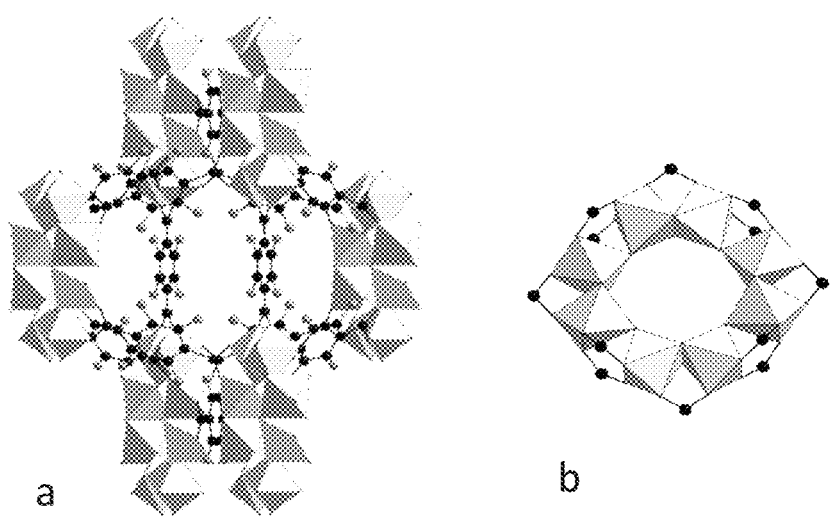
FIGS. 4a and 4b shows the crystallographic structure of a material obtained as per example 2 in accordance with one embodiment.

The crystallographic structure of the material obtained is represented schematically in the appended FIG. 4, in which the crystalline structure of the material along the axis a (or b) (FIG. 4a) and also a view of a wheel of titanium octahedra (carbon atoms: black points; nitrogen atoms: grey points) have been represented. The material crystallizes in the orthorhombic space group I4/mmm (No. 139) with the following parameters:

a=18.673(1) Å, c=18.139(1) Å, lattice volume: 6324.5(1) Å3.

This material is constituted of octahedra of titanium oxide TiO$_5$(OH) which assemble into aggregates (or wheels) of eight octahedra connected together by 2-aminoterephthalate anions (FIGS. 4a and 4b). The whole assembly defines a pseudo-cubic porous solid with a three-dimensional network of pores. The structure may also be described as an assembly of hybrid "octahedra" with, on each apex of each octahedron, a wheel constituted of eight titanium polyhedra. The apertures for access to the pores have a free dimension close to 5 to 6 Angströms and two types of cages are present, having dimensions close to 6 to 13 Angströms respectively. The amino group is disordered over 4 crystallographic positions and an occupation of 25% was attributed to the nitrogen atom of the amino group.

The atomic coordinates of this material are given in table 5 below (hydrated phase):

TABLE 5

| Atom | Wyckoff position | Degree of occupation | x/a | y/b | z/c |
|---|---|---|---|---|---|
| Ti | 16l | | 0.20487 | 0.07254 | 1/2 |
| O1 | 16l | | 0.31087 | 0.05903 | 1/2 |
| O2 | 16n | | 0.19180 | 0 | 0.42820 |
| O3 | 32o | | 0.22350 | 0.13977 | 0.42966 |
| O4 | 8h | | 0.10766 | 0.10766 | 1/2 |
| C1 | 8j | | 0.34876 | 0 | 1/2 |
| C2 | 8j | | 0.42505 | 0 | 1/2 |
| C3 | 16l | | 0.46289 | 0.07112 | 1/2 |
| N1 | 16l | 25% | 0.40989 | 0.13166 | 1/2 |
| C4 | 16m | | 0.19137 | 0.19137 | 0.40513 |
| C5 | 16m | | 0.22438 | 0.22438 | 0.32907 |
| C6 | 32o | | 0.18500 | 0.28300 | 0.28828 |
| N2 | 32o | 25% | 0.32500 | 0.12500 | 0.33000 |
| Ow1 [a] | 8h | | 0.17979 | 0.17979 | 0 |
| Ow2 | 16m | 81% | 0.07677 | 0.07677 | 0.29254 |
| Ow3 | 16n | 83% | 0.38985 | 0 | 0.28589 |
| Ow4 | 2b | | 0 | 0 | 1/2 |
| Ow5 | 16m | 79% | 0.09328 | 0.09328 | 0.08084 |
| Ow6 | 32o | 84% | 0.24910 | 0.06480 | 0.10202 |
| Ow7 | 16n | 84% | 0.24188 | 0 | 0.24106 |
| Ow8 | 4e | | 0 | 0 | 0.17823 |
| Ow9 | 4e | | 0 | 0 | 0.64063 |
| Ow10 | 2a | | 0 | 0 | 0 |

[a] In this table, the water molecules are denoted Owi (i = 1 to 10) and are not, strictly speaking, a part of the structure of the material since they only fill its pores when it is exposed to ambient air.

The main interatomic distances, expressed in Ångströms, are given in table 6 below:

TABLE 6

| Ti | O3 | x, y, z | 1.82(1) |
|---|---|---|---|
| | O3 | x, y, 1 − z | 1.82(1) |
| | O2 | x, −y, 1 − z | 1.90(1) |
| | O2 | x, y, z | 1.90(1) |
| | O4 | x, y, z | 1.93(1) |
| | O1 | x, y, z | 2.00(1) |
| C1 | O1 | x, −y, 1 − z | 1.31(1) |
| | O1 | x, y, z | 1.31(1) |
| | C2 | x, y, z | 1.43(1) |
| C2 | C1 | x, y, z | 1.43(1) |
| | C3 | x, −y, 1 − z | 1.50(1) |
| | C3 | x, y, z | 1.50(1) |
| C3 | C3 | 1 − x, y, 1 − z | 1.39(1) |
| | N1 | x, y, z | 1.50(1) |
| | C2 | x, y, z | 1.50(1) |
| N1 | C3 | x, y, z | 1.50(1) |
| C4 | O3 | y, x, z | 1.22(1) |
| | O3 | x, y, z | 1.22(1) |
| | C5 | x, y, z | 1.63(1) |
| C5 | C6 | x, y, z | 1.51(1) |
| | C6 | y, x, z | 1.51(1) |
| | C4 | x, y, z | 1.63(1) |
| C6 | C5 | x, y, z | 1.51(1) |
| | N2 | y, x, z | 1.56(1) |
| | C6 | 0.5 − y, 0.5 − x, 0.5 − z | 1.63(1) |
| N2 | C6 | y, x, z | 1.56(1) |

Figure 5:
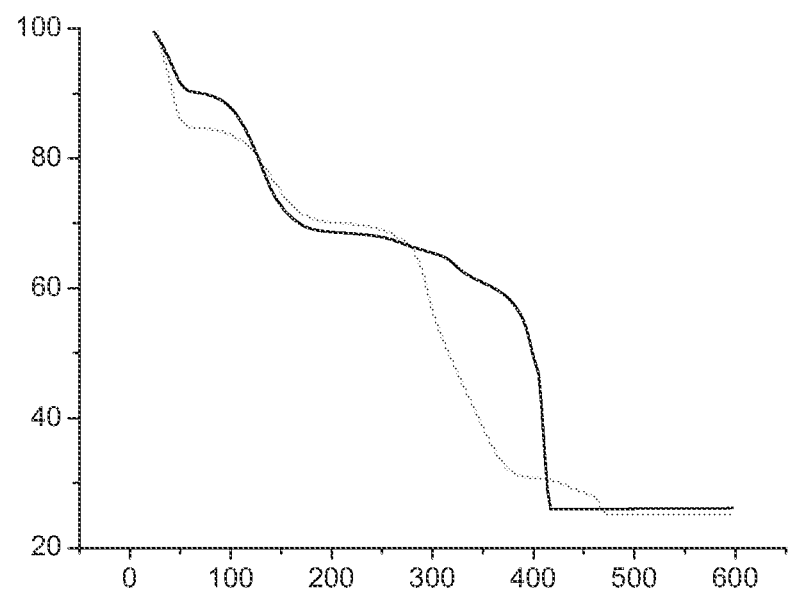
FIG. 5, a chart of a thermogravimetric analysis of the material prepared as per examples 1 (black) and 2 (grey) in accordance with one embodiment.

The results of the thermogravimetric analysis of the material prepared in this example, and also those of the TiBDC material prepared above in example 1 were carried out on the TA2050 machine and are given in appended FIG. 5. In this figure, the mass (expressed as a percentage) is a function of the temperature (expressed in ° C.). The black curve corresponds to the TiBDC from example 1 and the grey curve corresponds to the Ti—NH$_2$BDC from example 2.

In this figure, it is observed that the TiBDC material has two characteristic losses of mass that correspond to the successive departure of the solvents contained in the pores, firstly of methanol between 25° C. and 100° C. then of DMF between 100 and 200° C.

The degradation of the material takes place at around 400° C. during the departure of the carboxylic acid constituting the framework. The residual solid is anatase TiO$_2$.

The same thermal behavior is observed for the Ti—NH$_2$BDC material with, as the only significant difference, a degradation of the framework at a lower temperature (300° C.). The residual solid is also anatase TiO$_2$.

Figure 6:
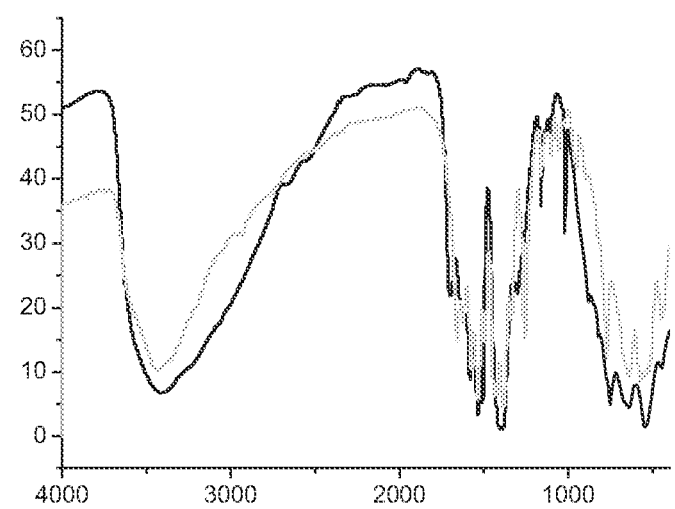
FIG. 6 is a chart for the IR spectra of the TiBDC and Ti—$NH_2$BDC materials as per examples 1 (black) and 2 (grey) in accordance with one embodiment.

The IR spectra of the TiBDC and Ti—NH$_2$BDC materials are represented in appended FIG. 6, in which the intensity (in arbitrary units) is a function of the wavelength (in cm$^{-1}$). In this figure, the black curve corresponds to the spectrum of TiBDC from example 1 and the grey curve corresponds to the spectrum of Ti—NH$_2$BDC from example 2. Observed for each of the two materials are the characteristic bands of the metal-carboxylate bonds (bands at around 1380 and 1600 cm$^{-1}$), a broad band at around 3400 cm$^{-1}$ corresponding to the free solvent molecules present in the pores, and also structural bands of the mineral part (O—Ti—O) at low wave numbers (400-800 cm$^{-1}$).

The results of the specific surface area measurements of the TiBDC and Ti—NH$_2$BDC materials are listed in table 7 below:

TABLE 7

| Material | BET method specific surface area (m$^2$·g$^{-1}$) | Langmuir method specific surface area (m$^2$·g$^{-1}$) | Microporous volume (cm$^3$·g$^{-1}$)* |
|---|---|---|---|
| TiBDC | 1550(20) | 1950(10) | 0.64(1) |
| Ti—NH$_2$BDC | 1200(20) | 1550(10) | 0.48(1) |

*calculated according to the t-plot method

Example 3

Demonstration of the Importance of the Choice of a Mixture of Solvents

In this example, the effect of the choice of the solvent medium on the nature of the materials synthesized from titanium isopropoxide and 1,4-benzenedicarboxylic acid was compared.

The syntheses were carried out in a pure solvent medium (methanol, DMF or isopropanol) or else in a methanol/DMF mixture.

a) Synthesis in a Pure Methanol Medium (Comparative Example that is not Part of the Invention)

0.4 mmol of 1,4-benzenedicarboxylic acid (60 mg) (Aldrich, 98%) then 0.35 mmol of titanium isopropoxide Ti(O-iPr)$_4$ (0.1 ml) (Acros Organics, 98%), were introduced into a Teflon® body containing 3 ml of methanol (Aldrich, 99.9%). The mixture was stirred for 5 minutes at ambient temperature. The Teflon® body was then introduced into a PAAR metallic body then placed in an oven at 150° C. for 15 hours. After returning to ambient temperature, the solid obtained was recovered by filtration, washed with acetone twice and dried in air.

b) Synthesis in a Pure Dimethylformamide Medium (Comparative Example that is not Part of the Invention):

1.0 mmol of 1,4-benzenedicarboxylic acid (166 mg) (Aldrich, 98%) then 1 mmol of titanium isopropoxide Ti(OiPr)$_4$ (0.2 ml) (Acros Organics, 98%), were introduced into a Teflon® body containing 5 ml of anhydrous DMF (Acros Organics). The mixture was stirred for 5 minutes at ambient temperature. The Teflon® body was then introduced into a PAAR metallic body then placed in an oven at 150° C. for 15 hours. After returning to ambient temperature, the solid was recovered by filtration, washed with acetone twice and dried in air.

c) Synthesis in a Pure Isopropanol Medium (Comparative Example that is not Part of the Invention):

0.35 mmol of 1,4-benzenedicarboxylic acid (60 mg) (Aldrich, 98%) then 0.5 mmol of titanium isopropoxide Ti(OiPr)$_4$ (0.1 ml) (Acros Organics, 98%), were introduced into a Teflon® body containing 5 ml of isopropanol (Aldrich, 99%). The mixture was stirred for 5 minutes at ambient temperature. The Teflon® body was then introduced into a PAAR metallic body then placed in an oven at 150° C. for 12 hours. After returning to ambient temperature, the solid was recovered by filtration, washed with acetone twice and dried in air.

d) Synthesis in a DMF/Methanol Mixture (Example in Accordance with the Invention):

1.5 mmol of 1,4-benzenedicarboxylic acid (250 mg) (Aldrich, 98%) then 1 mmol of titanium isopropoxide Ti(OiPr)$_4$ (0.3 ml) (Acros Organics, 98%), were introduced into a Teflon® body containing 4.5 ml of anhydrous DMF (Acros Organics) and 0.5 ml of methanol (Aldrich, 99.9%). The mixture was stirred for 5 minutes at ambient temperature. The Teflon® body was then introduced into a PAAR metallic body then placed in an oven at 150° C. for 15 hours. After returning to ambient temperature, the solid was recovered by filtration, washed with acetone twice and dried in air.

Figure 7:
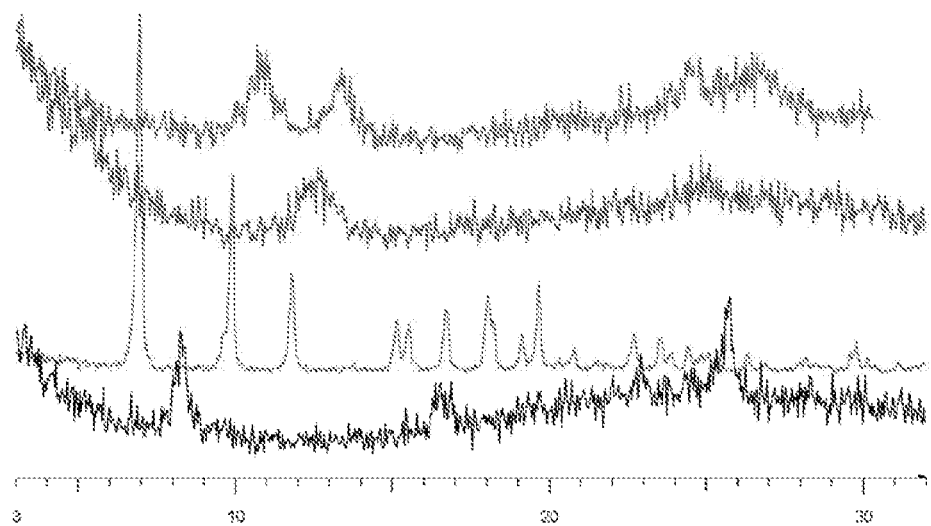
FIG. 7 is a XRD diffraction diagram as per example 3 in accordance with one embodiment.

The XRD diffraction diagrams ($\lambda$Cu=1.5406 Å) of the powders thus obtained in each of the solvent media are represented in appended FIG. 7, in which the intensity (in arbitrary units) is a function of the diffraction angle (in degrees). In this figure, the highest curve corresponds to the synthesis carried out in pure methanol, the next curve corresponds to the synthesis carried out in pure isopropanol, and the lowest curve corresponds to the synthesis carried out in pure DMF. The curve situated just above the lowest curve is very different from the three other curves and it corresponds to the synthesis carried out in the methanol/DMF mixture. It is observed that the materials obtained in a pure solvent medium are very poorly crystallized, their XRD diffractograms are completely different from that of the TiBDC material obtained above in example 1 (see appended FIG. 1) and from that obtained when the synthesis is carried out in the methanol/DMF mixture. Their diffraction peaks are also located at larger angles, which expresses a greater density of the network and therefore a lower porosity.

All conditions otherwise being equal (nature of the precursors, synthesis times and temperatures), these tests demonstrate that the nature of the phase formed depends strongly on the choice of solvent. The use of a reaction medium constituted of a single solvent, as described, for example, in international application WO 2007/118888 does not make it possible to result in a material in accordance with the invention. Only the use of a mixture constituted of at least two solvents in accordance with the process of the invention, such as for example a mixture of methanol and dimethylformamide, makes it possible to obtain a TiBDC material that is perfectly organized in the form of a very well crystallized tetragonal porous phase.

Example 4

Demonstration of the Importance of the Choice of the Titanium Precursor

In this example, the effect of the choice of the titanium precursor on the structure of the material synthesized was studied. The syntheses were carried out in a pure DMF medium or else in a methanol/DMF mixture starting from titanium tetrachloride (titanium precursor not in accordance with the invention) and 1,4-benzenedicarboxylic acid.

a) Synthesis in a Pure DMF Medium

This synthesis was carried out according to the protocol described in example 4 from application WO 2007/118888.

52 mmol of 1,4-benzenedicarboxylic acid (8.72 g) (Aldrich, 98%) then 52 mmol of titanium tetrachloride TiCl$_4$ (10 g) were introduced into a 500 ml round-bottomed flask containing 300 ml of anhydrous DMF (Acros Organics). The reaction mixture was stirred for 18 hours at 130° C. until a precipitate was obtained. The precipitate was recovered by centrifugation, then washed 3 times with 50 ml of DMF then 3 times with 50 ml of methanol. The precipitate was then dried at 160° C. for 16 hours.

The analyses carried out reveal that the particles of the powder obtained are not very porous (BET specific surface area: 107 m$^2$/g) and are amorphous (XRD).

b) Synthesis in a DMF/Methanol Medium

The synthesis described in detail above in a) was reproduced, but using, as solvents, a mixture constituted of 240 ml of anhydrous DMF and 60 ml of methanol.

The analyses carried out also reveal that the particles of the powder obtained are not very porous and are amorphous (XRD).

These tests demonstrate that it is not possible to result in a material having a pseudo-cubic crystalline structure in accordance with the present invention using titanium tetrachloride as titanium precursor in place of a titanium alkoxide of formula (I), regardless of the solvent medium used during the synthesis (pure DMF medium or mixture of DMF and of methanol).

Example 5

Preparation of a Titanium MOF Starting From a Preformed Titanium Oxo Complex

In this example, a hybrid material of formula Ti$_8$O$_8$(OH)$_4$ [O$_2$C—C$_6$H$_4$—CO$_2$]$_6$ were synthesized using, as titanium precursor, a titanium oxo cluster of formula Ti$_{16}$O$_{16}$(OEt)$_{32}$.

1) First Step: Synthesis of the Titanium Oxo Complex of Formula Ti$_{16}$O$_{16}$(OEt)$_{32}$ The Ti$_{16}$O$_{16}$(OEt)$_{32}$ oxo complex was obtained by controlled hydrolysis, under sub-stoichiometric conditions, in water (H$_2$O/Ti=0.5) of the titanium alkoxide Ti(OEt)$_4$ in absolute ethanol. A reaction mixture composed of 7 ml of Ti(OEt)$_4$, 7 ml of absolute ethanol and 300 μl of water was treated in a solvothermal medium for 15 days at 100° C., The crystallization of the titanium oxo complex was initiated by slow cooling of the reaction mixture (cooling rate: 1° C./hours). The titanium oxo complex in crystallized form was then recovered after filtration with a yield of 70%.

Figure 8:
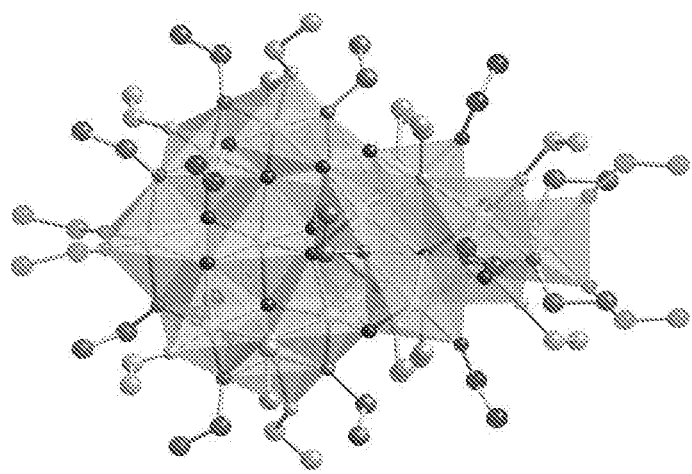
FIG. 8 shows the crystalline structure of the oxo complex as per example 5, in accordance with one embodiment.

The crystalline structure of the oxo complex was determined by single-crystal X-ray diffraction. It is represented schematically in appended FIG. 8. The determining of the structure made it possible to demonstrate the formation of a lattice formed of two orthogonal blocks of 8 titanium oxo complexes each, acknowledging a pseudo axis of −4 inverse rotation. The 16 titanium atoms are connected by three different types of oxo bridges, 4 oxygens being bonded twice to the metal centers [μ$_2$-O], 8 being bonded three times to titanium [μ$_3$-O] and 4 being bonded four times to titanium [μ$_4$-O]. At the surface of the oxo core is a crown of 32 ethoxides, 16 of them are end groups, the other 16 are bridging groups.

This structure is described in detail in the articles by A. Mosset et al., C. R. Acad, Sci. Paris, t.307, Series II, 1988, p. 1747-1750 and by J. Galy et al. Chem. Soc. Dalton Trans., 1991, p. 1999.

2) Second Step: Synthesis of the Hybrid Material of Formula $Ti_8O_8(OH)_4[O_2C—C_6H_4—CO_2]_6$ 0.17 g of the titanium oxo complex $Ti_{16}O_{16}(OEt)_{32}$ obtained above in the preceding step and 0.27 g of terephthalic acid were introduced into a mixture of 4 ml of DMF and 1 ml of methanol. The reaction mixture was placed in an autoclave at 150° C. for 20 hours. The precipitate obtained was filtered, washed 3 times with DMF then dried for 20 h at 150° C. The yield of the reaction was 74%.

A hybrid material identical in every respect to that from example 1 was obtained.

Example 6

Preparation of a Titanium MOF From a Preformed Titanium Oxo Complex

In this example, a hybrid material of formula $Ti_8O_8(OH)_4[O_2C—C_6H_4—CO_2]_6$ was synthesized using, as titanium precursor, a titanium oxo cluster of formula $Ti_8O_8(OOC(CH_3)_3)_{16}$.

1) Second Step: Synthesis of the Titanium Oxo Complex of Formula $Ti_8O_8(OOC(CH_3)_3)_{16}$ The molecular complex of formula $Ti_8O_8(OOCC(CH_3)_3)_{16}$ was obtained under solvothermal conditions (24 hours at 100-110° C. in an autoclave) by the reaction of 2 ml of $Ti(OiPr)_4$ with 7 g of pivalic acid ($HOOCC(CH_3)_3$) in 50 ml of acetonitrile. The titanium oxo complex thus formed in crystallized form was then recovered after filtration with a yield of 94%.

Figure 9:
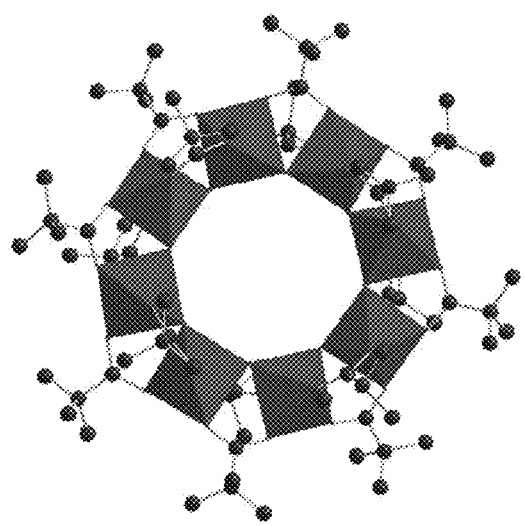
FIG. 9 shows the crystalline structure of the oxo complex as per example 6, in accordance with one embodiment.

The crystalline structure of the oxo complex was determined by single-crystal X-ray diffraction. It is represented schematically in appended FIG. 9. The determining of the structure made it possible to demonstrate the formation of a crown of eight octahedral titanium oxo complexes connected by apexes, and of 16 bidentate bridging carboxylate groups. Eight carboxylate groups are placed in equatorial position, the other eight in axial position (4 on each side of the plane formed by the crown of the oxo core).

2) Second Step: Synthesis of the Hybrid Material of Formula $Ti_8O_8(OH)_4[O_2C—C_6H_4—CO_2]_6$ 0.6 g of the titanium oxo complex $Ti_8O_8(OOCC(CH_3)_3)_{16}$ obtained above in the preceding step and 1.55 g of terephthalic acid were introduced into a mixture constituted of 18 ml of DMF and 4.5 ml of methanol. This reaction mixture was placed in an autoclave at 110° C. for 4 days. The precipitate obtained was filtered, washed 3 times with DMF then dried for 20 h at 150° C. The yield of the reaction was 97%.

A hybrid material identical in every respect to that from example 1 was obtained.

Example 7

Preparation of a Hybrid Material of Formula $Ti_8O_8(OH)_4[O_2C—C_4H_2S—CO_2]_6$ from the Material of Formula $Ti_8O_8(OH)_4[O_2C—C_6H_4—CO_2]_6$ In this example, a hybrid material of formula $Ti_8O_8(OH)_4[O_2C—C_4H_2S—CO_2]_6$, that is say a hybrid material constituted of subunits of formula (I) in accordance with the invention, in which X represents a thiophene ring, were synthesized by exchange of the organic spacer starting from the material prepared in example 1 above, that is to say a hybrid material constituted of subunits of formula (I) in which X is a benzene ring.

1 g of the material of formula $Ti_8O_8(OH)_4[O_2C—C_6H_4—CO_2]_6$ obtained above in example 1 and 5 g of thiophene dicarboxylate were dispersed in a mixture constituted of 40 ml of DMF and 10 ml of methanol. This dispersion was placed under solvothermal conditions at 150° C. for 16 hours. After cooling, the powder obtained of the expected crystallized material was filtered, washed 3 times with DMF and dried for 6 hours at 150° C. The yield of this exchange reaction was 93%.

This example shows that it is possible to attain crystallized hybrid materials by simple exchange of the organic spacers.

Example 8

Synthesis of a TiO-BDC phase of $TiO[O_2C—C_6H_4—CO_2]$ Composition 1.5 mmol of 1,4-benzenedicarboxylic acid (250 mg) (Aldrich, 98%) then 1 mmol of titanium isopropoxide $Ti(OiPr)_4$ (0.3 ml) (Acros Organics, 98%), were introduced into a Teflon® body containing 5 ml of a mixture constituted of 2.5 ml of anhydrous dimethylformamide (Acros Organics) and 2.5 ml of methanol (Aldrich, 99.9%). The reaction mixture was stirred for 5 minutes at ambient temperature.

The Teflon® body was then introduced into a PAAR metallic body then put into an oven at 150° C. for 15 hours. After returning to ambient temperature, the expected material in the form of a white solid was recovered by filtration, washed with acetone twice and dried in air. A crystallized phase, denoted TiO-BDC.

Figure 10:
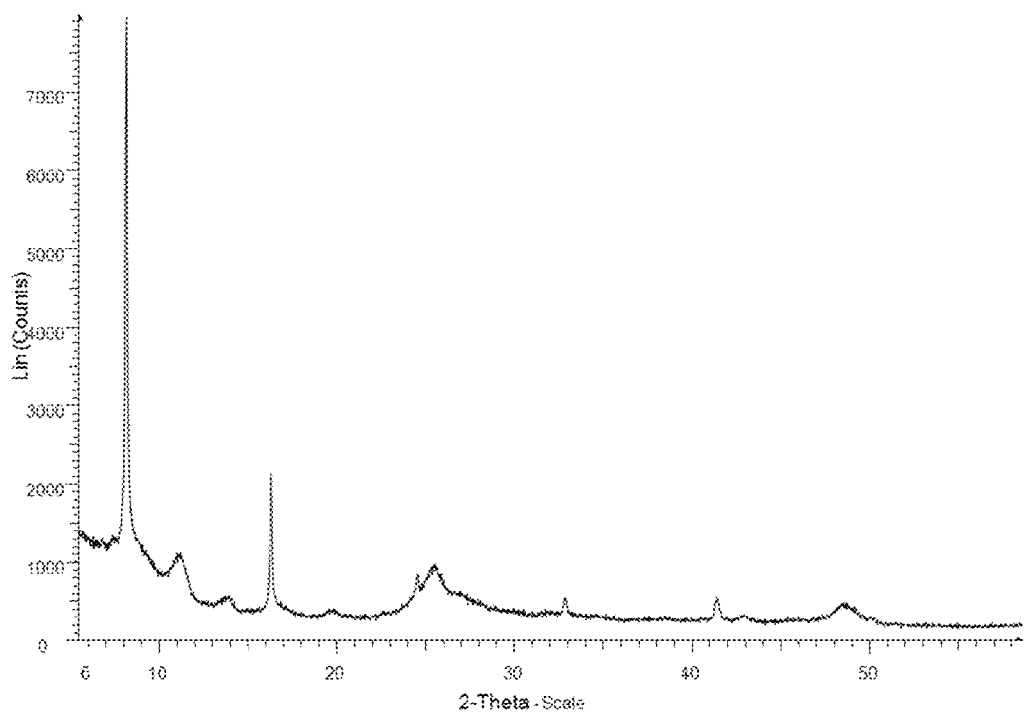
FIG. 10 is a XRD diffraction diagram as per example 8 in accordance with one embodiment.

The XRD diffraction diagram is represented in appended FIG. 10, in which the intensity (expressed in arbitrary units) is a function of the diffraction angle in degrees.

The specific surface area measurements of this material, carried out on a 20 mg sample previously activated under primary vacuum ($10^{-3}$ Torr) for 15 hours at 150° C., make it possible to calculate a BET surface area of 250(15) $m^2 \cdot g^{-1}$.

The thermal stability of the solid was evaluated. The XRD diffractogram was collected with a diagram every 20° C. in air (not represented). The TiO-BDC solid was found to be stable up to a temperature of 300° C.

Example 9

Synthesis of a Ti-BDC(2OH) Phase of $TiO[O_2C—C_6H_2(OH)_2—CO_2]$ Composition 0.67 mmol of 2,5-dihydroxy-1,4-dicarboxylie acid (150 mg) (Aldrich, 98%) then 0.33 mmol of titanium isopropoxide $Ti(OiPr)_4$ (0.1 ml) (Acros Organics, 98%), are introduced into a solution containing 2.5 ml of dimethylformamide (Acros Organics, extra-dry) and 2.5 ml of methanol (Aldrich, 99.9%). The mixture was stirred for 5 minutes at ambient temperature.

Figure 11:
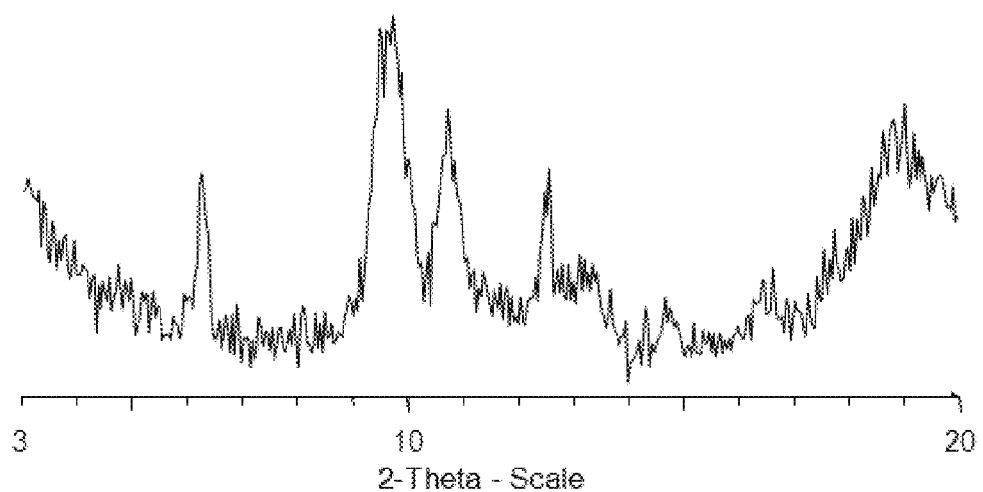
FIG. 11 is XRD diffractogram as per example 9 in accordance with one embodiment.

The Teflon body was then introduced into a PAAR metallic body then placed in an oven at 200° C. for 15 hours. After returning to ambient temperature, the solid of bright orange color was recovered by filtration, washed with acetone twice and dried in air. An orangey crystallized phase, referred to as Ti-BDC(2OH) was obtained, the XRD diffractogram of which is represented in appended FIG. 11, in which the intensity, in arbitrary units, is a function of the diffraction angle in degrees.

The specific surface area measurements of this material, carried out on a 20 mg sample previously activated under primary vacuum ($10^{-3}$ Torr) for 15 hours at 200° C., made it possible to calculate a BET surface area of 980(15) $m^2 \cdot g^{-1}$.

Figure 12:
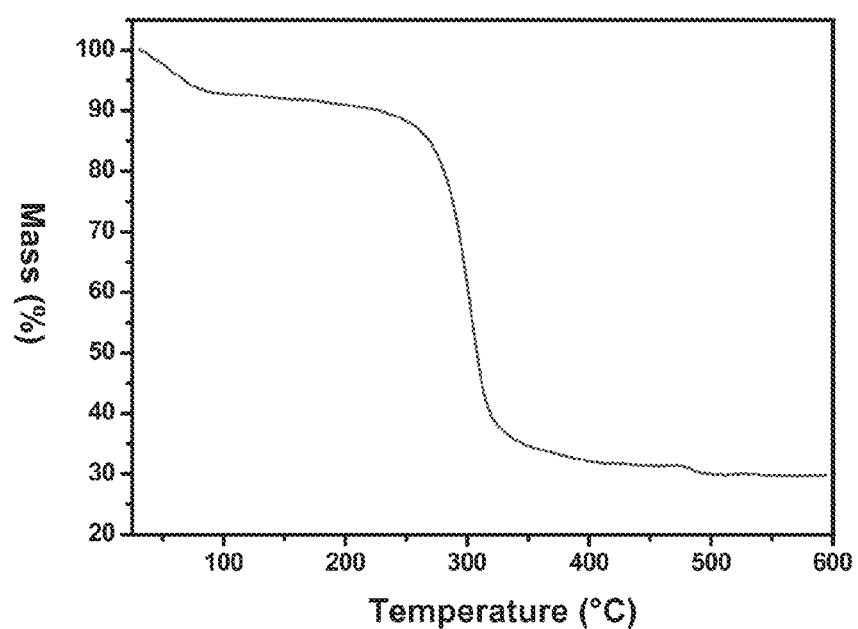
FIG. 12 chart for the results of the thermogravimetric analysis of the material prepared in example 9 in accordance with one embodiment.

The results of the thermogravimetric analysis of the material prepared in this example, carried out on the STA6000 machine, are given in appended FIG. 12. In this figure, the mass (expressed as a percentage) is a function of the temperature (expressed in ° C.). The losses calculated, starting from a formula $TiO[O_2C—C_6H_2(OH)_2—CO_2].H_2O$, are respectively 6.8% (free water) and 62.7%, in very good agreement with the experimental losses (around 7 and 63% respectively). This experiment also showed that the Ti-BDC(2OH) material is stable in air up to 205° C.

Example 10

Use of the Ti—NH$_2$BDC Phase for Storing Carbon Dioxide

In this example, the adsorption/desorption capacity, with respect to carbon dioxide, of the Ti—NH$_2$BDC phase prepared in example 2 above was tested.

The $CO_2$ absorption properties of the Ti—NH$_2$BDC phase were tested using a Hiden Isochema IGA gravimetric machine.

30 mg of the Ti—NH$_2$BDC solid were introduced onto the balance and activated firstly under secondary vacuum ($10^{-6}$ Torr) at ambient temperature for 1 hour then at 200° C. for 15 hours. The adsorption/desorption capacity was tested at various temperatures: 10, 20, 30 and 40° C. For each temperature, the $CO_2$ was introduced at variable pressure, between 50 mbar and 20 bar, and the mass of the solid charged with $CO_2$ was measured as soon as equilibrium was attained (maximum duration of 30 minutes). By deducting the initial mass of dry solid, the amount of $CO_2$ adsorbed into the pores of the material was thus able to be calculated. Between two measurements at different temperatures, the solid was degassed overnight at 150° C. under secondary vacuum.

Figure 13:
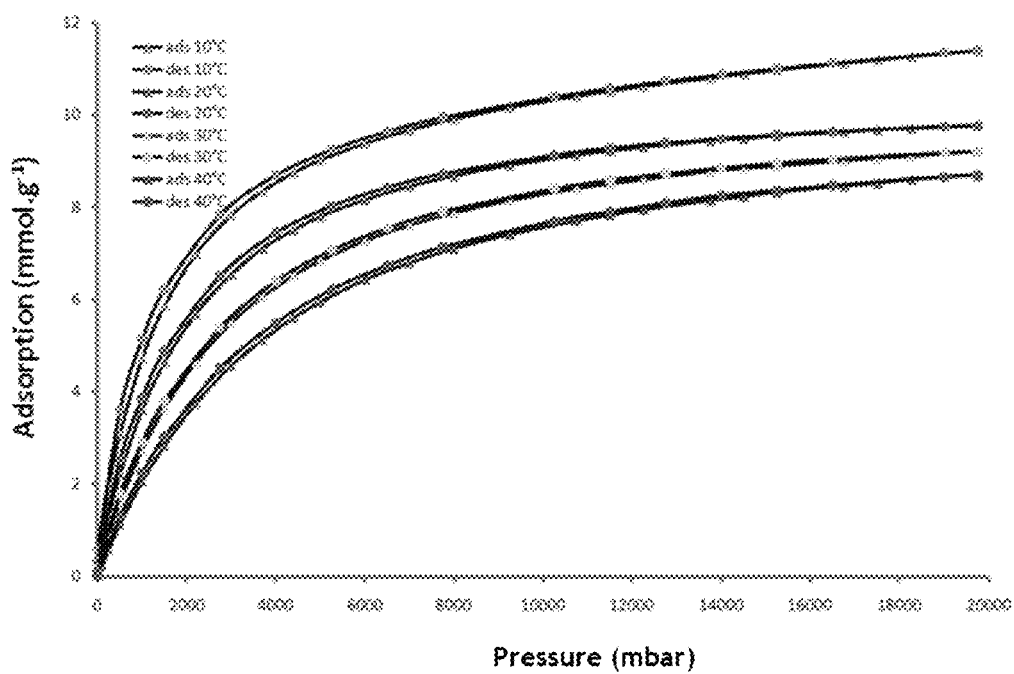
FIG. 13 is a chart showing the amount of carbon dioxide adsorbed (in minag) as a function of the pressure (in mbar) as per example 10 in accordance with one embodiment.

The results obtained are represented in appended FIG. 13, in which the amount of carbon dioxide adsorbed (in $mmol \cdot g^{-1}$) is a function of the pressure (in mbar). In this figure, the various pairs of curves, starting from the highest curve and going toward the lowest curve, respectively represents the adsorption (solid triangles) and the desorption (solid circles) of $CO_2$ at 10, 20, 30 and 40° C. The results presented in this figure show that the material from example 2 is capable of adsorbing large amounts of $CO_2$ with a remarkable affinity at low pressure, symbolized by the absorption of close to 3.8 $mmol \cdot g^{-1}$ of $CO_2$ at 20° C. under 1 bar of pressure.

Example 11

Synthesis of the Ti—NH$_2$BDC Phase According to a Process in Which the Heating Step is Carried Out in a Microwave Oven In this example, the Ti—NH$_2$BDC phase was synthesized according to a process in which the second step was carried out by heating in a microwave oven.

1.66 mmol of 2-aminoterephthalic acid (300 mg) (Aldrich, 98%) then 273 mg of titanium oxo cluster $Ti_8O_8(OOC(CH_3)_3)_{16}$ were introduced into a solution containing 5 ml of dimethylformamide (Acros Organics, 99%) and 1 ml of methanol (Aldrich, 99.9%). The reaction mixture was stirred for 1 minute at ambient temperature.

The Teflon body (100 ml capacity) was then introduced into a microwave oven (CEM, Mars 300, equipped with a 14-reactor carousel) and a power of 400 W was applied with a temperature rise of 2 minutes up to 150° C. A hold of 15 minutes was observed at this temperature and at this power. After returning to ambient temperature, the yellow solid thus obtained was recovered by filtration, washed with acetone twice and dried in air.

Figure 14:
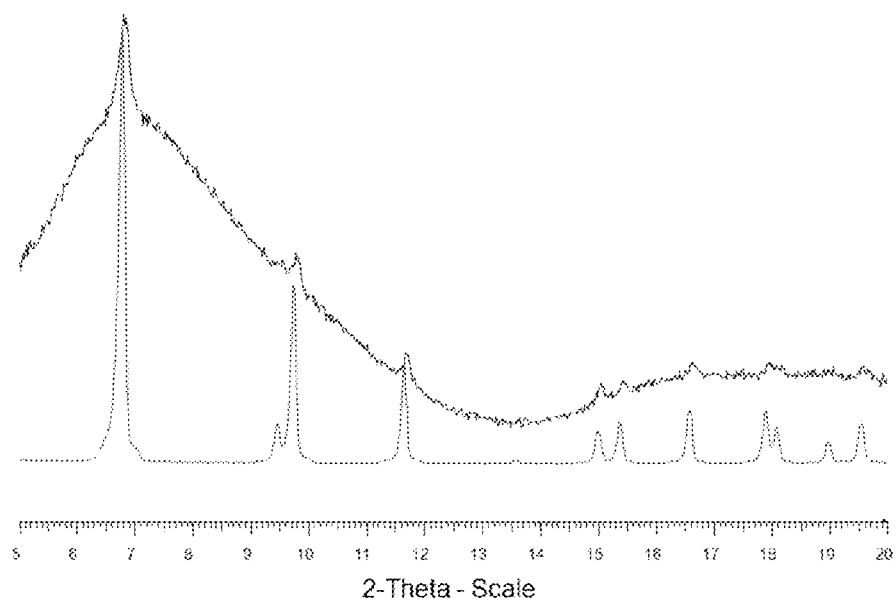
FIG. 14 is a XRD diffraction diagram as per example 11 in accordance with one embodiment.

The XRD diffraction diagram of the material obtained is represented in appended FIG. 14, in which the intensity (in arbitrary units) is a function of the diffraction angle (in degrees) (top curve). By way of comparison, the spectrum of the Ti—NH$_2$BDC material obtained above in example 2 is also represented in FIG. 14 (bottom curve).

The significant broadening of the diffraction lines shows that the product obtained by the microwave method has a particle size much smaller than that of the solid obtained by the solvothermal route.

Example 12

Demonstration of the Photochromic and Photocatalytic Properties of the TiBDC Phase 0.025 g of TiBDC were immersed in 0.015 ml of benzyl alcohol then subjected to UV irradiation at a wavelength of 350 nm for 15 minutes under a stream of nitrogen.

The same experiment was carried out on a commercial $TiO_2$ powder sold under reference P25 by Degussa.

Figure 15:
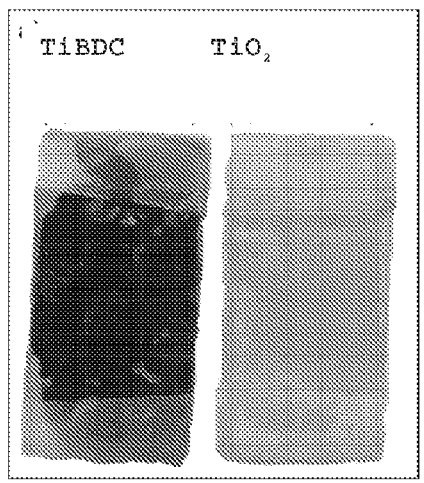
FIG. 15 is a photograph of the materials after impregnation by benzyl alcohol and UV irradiation as per example 12 in accordance with one embodiment.

Appended FIG. 15 shows a photograph of these two materials after impregnation by benzyl alcohol and UV irradiation. A spontaneous and intense coloration of the TiBDC material of dark grey/blue is observed. This rapidly observed photochromic effect is due to the reduction of the titanium (IV) centers to titanium (III).

On the contrary, only a very weak coloration of the $TiO_2$ powder was observed.

The coloration intensity of the TiBDC material soaked with benzyl alcohol is explained by a large number of photoactive sites capable of being stabilized in Ti(III) form.

Figure 16:
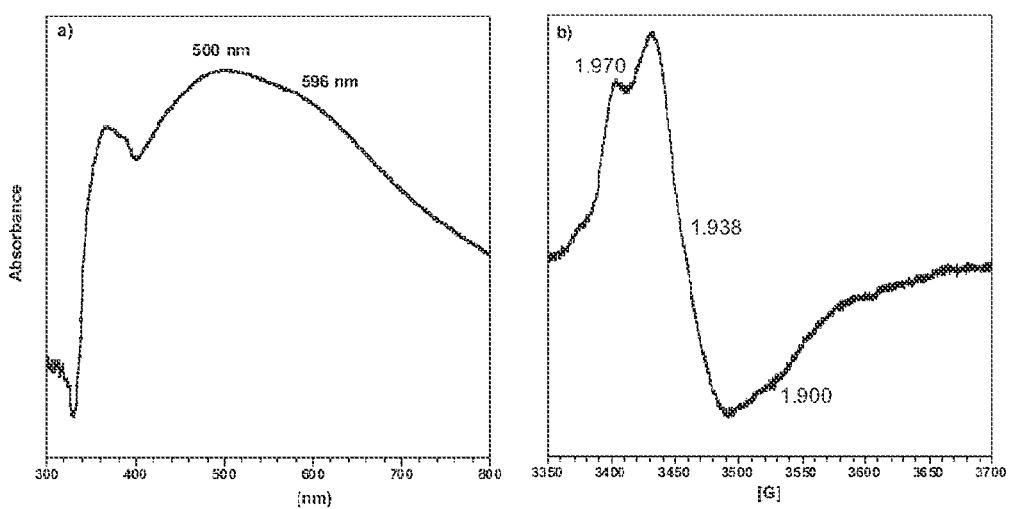
FIGS. 16a and 16b are graphs representing the UV spectrum (and the electron paramagnetic resonance (EPR) of the TiBDC material after impregnation and UV irradiation as per example 12 in accordance with one embodiment.

Appended FIG. 16 represents the IIV spectrum (FIG. 16*a*: absorbance as a function of the wavelength in nm) and the electron paramagnetic resonance (EPR) spectrum at 75 K of the TiBDC material after impregnation and UV irradiation (FIG. 16*b*: derived absorption as a function of the magnetic field (G)). The EPR spectrum makes it possible to demonstrate the existence of photoreduced paramagnetic titanium (III) sites.

The coloration of the samples is intense and stable in the absence of oxygen.

The stability of the coloration of the TiBDC material was observed over several weeks in the absence of oxygen, it is much greater than the coloration of conventional dense $TiO_2$ powders. This stability is explained by the presence of a large number of alcohol molecules in the vicinity of the photoreduced centers which will trap photoinduced holes, leading to the oxidation of the alcohol functions to aldehyde functions.

The photochromic behavior is reversible, the decoloration of the sample taking place gradually when the powder is placed in oxygen.

These two phenomena are concomitant: the photochromic character is due to the reduction of $Ti^{IV}$ to $Ti^{III}$ and the photocatalytic character is due to the oxidation of the absorbed molecules (for example alcohol to aldehyde).

Figure 17:
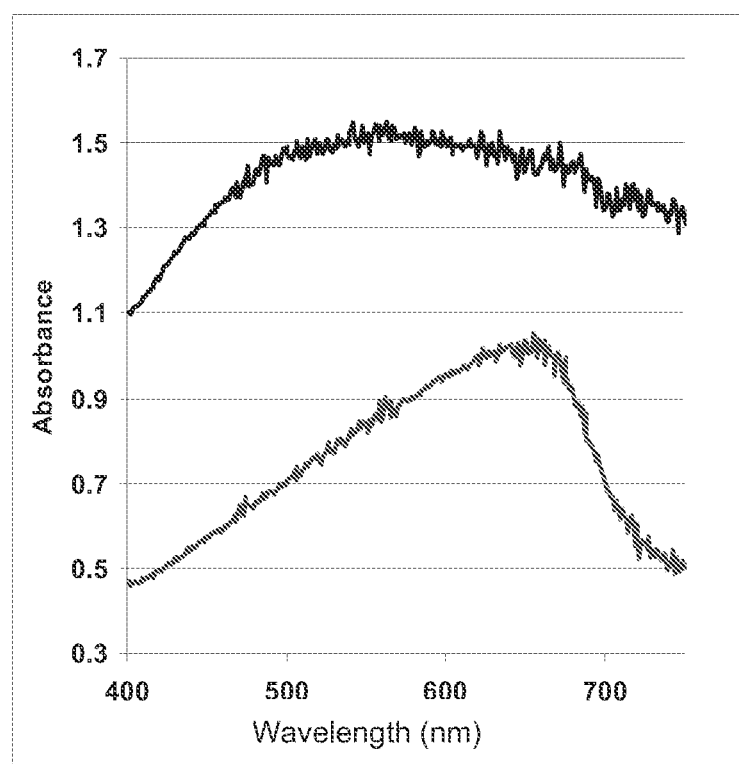
FIG. 17 is a chart representing the UV/visible absorption spectra of TiBDC (top curve) and of $TiO_2$ (bottom curve) after impregnation by benzyl alcohol and UV irradiation as per example 12 in accordance with one embodiment.

FIG. 17 represents the UV/visible absorption spectra of TiBDC (top curve) and of $TiO_2$ (bottom curve) after impregnation by benzyl alcohol and UV irradiation. In this figure, the absorbance is a function of the wavelength (in nm).

This example therefore demonstrates that the high and accessible specific surface area of the TiBDC material allows the easy absorption of organic molecules within the three-dimensional structure.

The materials in accordance with the invention can thus find applications in the field of laser marking, heterogeneous catalysis or else as an oxygen indicator material.

The invention claimed is:

1. An inorganic-organic hybrid solid material based on titanium, wherein said inorganic-organic hybrid solid material has a pseudo-cubic crystalline structure and that it is constituted exclusively of units of formula (I) below:

$$Ti_aO_b(OH)_c[(^-OOC)-X-\#]_d \qquad (I)$$

in which:
X is an organic spacer and represents a saturated or unsaturated, linear or branched, aliphatic chain having 2 to 12 carbon atoms; a monocyclic, bicyclic or tricyclic hydrocarbon-based aromatic group that is unsubstituted or that is substituted by one or more substituents independently chosen from a halogen atom and amino, nitro, hydroxyl, $C_1$-$C_4$ trifluoroalkyl and $C_1$-$C_4$ alkyl groups; a benzophenone group; a monocyclic or bicyclic heteroaromatic group in which the ring(s) is(are) 5- or 6-membered ring(s), said group containing at least one heteroatom chosen from nitrogen and sulfur and being unsubstituted or substituted by one or more substituents R independently chosen from a halogen atom and amino, nitro, hydroxyl, $C_1$-$C_4$ trifluoroalkyl and $C_1$-$C_4$ alkyl groups;
a and b, which are identical or different, are integers varying from 1 to 16 inclusively;
c and d, which are identical or different, are integers varying from 1 to 32 inclusively;
the indices a, b, c and d adhere to the relation 4a=2b+c+d;
the titanium atoms form a purely inorganic elementary building block constituted of titanium oxo complexes;
# is the point through which two units of formula (I) are joined together; # represents a covalent bond between a carbon atom belonging to the spacer X and the carbon atom of a carboxylate group $COO^-$ of another unit of formula (I) and in which the two oxygen atoms of the carboxylate group belong respectively to two adjacent octahedral titanium oxo complexes of an elementary building block of said other unit of formula (I);
said units of formula (I) together forming a three-dimensional structure and defining cavities having a free diameter of 4 to 40 Å that are accessible through triangular apertures having dimensions of 4 to 15 Å.

2. The material as claimed in claim 1, wherein the aliphatic chains defined for X are selected from the group consisting of $C_1$-$C_1$ alkyl chains and $C_2$-$C_4$ alkene or alkene chains.

3. The material as claimed in claim 1, wherein the hydrocarbon-based groups defined for X are selected from the group consisting of phenylene; chlorophenylene; bromophenylene; aminophenylene; nitrophenylene; mono-, di- or tetramethylphenylene: mono- or diethenylphenylene; mono- or dihydroxyphenylene; biphenylene; diphenyldiazene; naphthalene and anthracene groups.

4. The material as claimed in claim 1, wherein the heterocycles defined for X are selected from the group consisting of thiophene, bithiophene, pyridine, bipyridine and pyrazine rings.

5. The material as claimed in claim 1, wherein the subunit [$^-$OOC—X-#] is selected from the groups of formulae (II-1) to (II-13) consisting of:

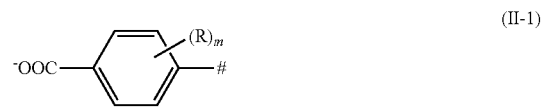
(II-1)

(II-2)

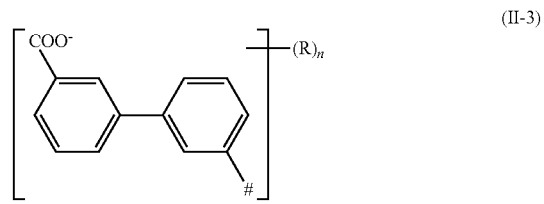
(II-3)

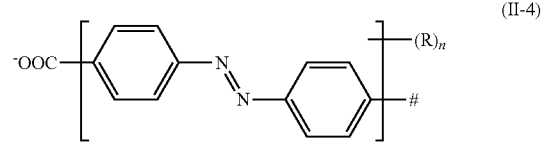
(II-4)

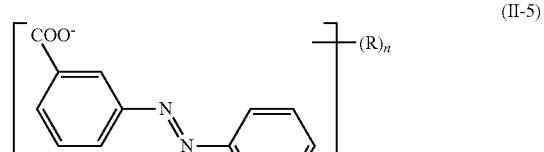
(II-5)

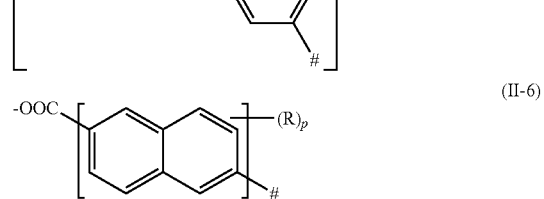
(II-6)

(II-7)

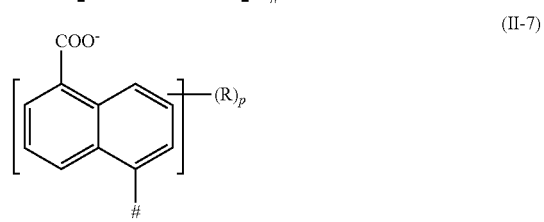
(II-8)

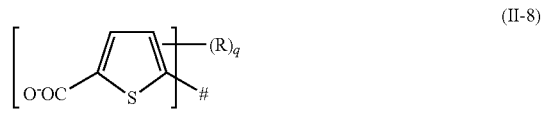
(II-9)

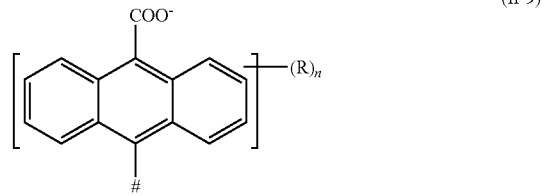

(II-10)

[structure: pyridine ring with O⁻OC on one side, (R)_r substituent, and # marker]

(II-11)

[structure: pyrazine ring with O⁻OC and (R)_q substituent, # marker]

(II-12)

O⁻OC—[CH₂—phenyl(R)_m—CH₂]—#

(II-13)

O⁻OC—[CH=CH—phenyl(R)_m—CH=CH]—# in which:
  R is a halogen atom, an amino, nitro, hydroxyl, $C_1$-$C_4$ trifluoroalkyl or $C_1$-$C_4$ alkyl group;
  m is an integer ranging from 0 to 4;
  n is an integer ranging from 0 to 8;
  p is an integer ranging from 0 to 6;
  q is an integer ranging from 0 to 2; and
  r is an integer ranging from 0 to 3.

6. The material as claimed in claim 5, wherein the subunit [⁻OOC—X-#] is selected from the group consisting of phenyl-1-carboxylate, phenyl-2-amino-1-carboxylate, phenyl-2,5-dihydroxy-1-carboxylate and thiophene-2-carboxylate.

7. The material as claimed in claim 1, wherein the units of formula (I) are selected from the subunits of formula (I-1) consisting of:

$$Ti_8O_8(OH)_4[(^-OOC)-X-\#]_{12} \quad (I-4)$$

in which:
  X and # are as defined above in claim 1;
  the titanium atoms form a purely inorganic elementary building block constituted of 8 octahedral titanium oxo complexes each comprising a central titanium atom surrounded by 6 oxygen atoms, said octahedral titanium oxo complexes being joined together either by a common edge, or by a common apex, in both cases by means of oxo-O— or hydroxo-OH— bridges; said building blocks being connected together in the three dimensions of space by organic spacers X; it being understood that each of the building blocks is connected to 12 organic spacers by means of carboxylate groups COO⁻ in which each of the two oxygen atoms is an integral part of two adjacent titanium oxo complexes.

8. The material as claimed in claim 1, wherein the cavities have a tree diameter of 5 to 12.6 Å.

9. The material as claimed in claim 1, wherein said material has a BET specific surface area of 200 to 6000 m²/g.

10. The material as claimed in claim 1, wherein said material has a pore volume of 0.1 to 3 cm³/g.

11. The use of a material as defined in claim 1, as a catalyst support for carrying out heterogeneously catalyzed chemical reactions or as a gas storage/separation/purification material or as a matrix for encapsulating active principles (medicaments, cosmetics) or else as a photochromic material for information storage, laser printing or as an oxygen indicator.

12. A process for preparing an inorganic-organic hybrid solid material based on titanium as defined in claim 1, wherein said process comprises the following steps:
  1) in a first step, a reaction mixture is prepared comprising:
    i) at least one titanium precursor chosen from titanium alkoxides of formula below:

$$Ti(OR_1)_4 \quad (III)$$

in which $R_1$ is a linear or branched alkyl radical comprising from 1 to 4 carbon atoms or at least one titanium oxo complex of formula (IV) below:

$$Ti_xO_y(OR_2)_z(OOCR_3)_w \quad (IV)$$

in which:
      $R_2$ represents a hydrogen atom, a linear or branched $C_1$-$C_6$ alkyl radical or a phenyl ring optionally substituted by one or more radicals chosen from a halogen atom, $C_1$-$C_4$ alkyl and $C_2$-$C_3$ alkene radical;
      $R_3$ represents a linear or branched $C_1$-$C_4$ alkyl radical, a $C_1$-$C_4$ trihaloalkyl radical or a phenyl ring;
      x is an integer ranging from 2 to 18:
      y is an integer ranging from 1 to 27;
      z is an integer ranging from 0 to 32;
      w is an integer ranging from 0 to 16;
      and in which the titanium atoms form an elementary building Hock constituted of a purely inorganic core of titanium oxo complexes in octahedral coordination each comprising a central titanium atom surrounded by 6 oxygen atoms, said octahedral titanium oxo complexes being joined together either by a common edge, or by a common apex, in both cases by means of oxo-O— or hydroxo-OH-bridges; said building blocks being surrounded by organic ligands of alcoholate ($OR_2$) and/or carboxylate ($OOCR_3$) type;
    ii) at least one dicarboxylic acid of formula (V) below:

$$HOOC-X'-COOH \quad (V)$$

in which X' represents a saturated or unsaturated, linear or branched, aliphatic chain having from 2 to 12 carbon atoms, a benzophenone group or a monocyclic, bicyclic or tricyclic hydrocarbon-based aromatic group that is unsubstituted or that is substituted by one or more substituents R' independently chosen from a halogen atom and amino, nitro, hydroxyl, $C_1$-$C_4$ trifluoroalkyl and $C_1$-$C_4$ alkyl groups;
    iii) a mixture of at least two organic solvents comprising at least one solvent S1 chosen from $C_1$-$C_4$ alcohols, benzyl alcohol and chlorobenzyl alcohol, and at least one solvent S2 selected from the group consisting of N,N-dimethylformamide, N,N-diethylformamide, dimethylsulfoxide, ethylene dioxane, acetonitrile, acetone, tetrahydrofuran, pyridine and N-methylpyrrolidone;
  2) in a second step, the reaction mixture thus obtained is brought to a temperature of 70 to 200° C., for 4 to 72 hours, until a precipitate corresponding to the expected solid material is obtained; then
  3) in a third step, the reaction mixture is cooled to ambient temperature;
  4) in a fourth step, the solid material is separated from the mixture of organic solvents;
  it being understood that when the solid material is constituted of units of formula (I) in which X is a monocyclic or bicyclic heteroaromatic group in which the ring(s)

is(are) optionally substituted 5- or 6-membered ring(s), said group containing at least one heteroatom selected from the group consisting of nitrogen and sulfur, then said process also comprises the following additional steps:

5) a fifth step of preparing a dispersion of the solid material resulting from the fourth step in at least one polar organic solvent, in the presence of at least one dicarboxylic acid of formula (VI) below:

HOOC—X"—COOH (VI)

in which X" represents a monocyclic or bicyclic heteroaromatic group in which the ring(s) is(are) 5- or 6-membered ring(s), said group containing at least one heteroatom selected from the group consisting of nitrogen and sulfur and being unsubstituted or substituted by one or more substituents R independently selected from the group consisting of a halogen atom and amino, nitro, hydroxyl, $C_1$-$C_4$ trifluoroalkyl and $C_1$-$C_4$ alkyl groups;

6) a sixth step, during which the dispersion thus obtained is brought to a temperature of 100 to 150° C. for a time of 4 hours to 4 days, which leads to the formation of a precipitate corresponding to the expected solid material; then 7) a seventh step during which the temperature is allowed to return to ambient temperature; and 8) an eighth step of separating the solid material thus obtained from the organic solvent(s).

13. The process as claimed in claim 12, wherein the precursors of formula (III) are selected from the group consisting of titanium ethoxide, titanium isopropoxide, titanium n-propoxide and titanium butoxide.

14. The process as claimed in claim 12, wherein the titanium oxo complexes of formula (IV) are chosen from $Ti_{16}O_{16}(OCH_2CH_3)_{32}$ and $Ti_8O_8(OOCR_3)_{16}$ in which $R_3$ is as defined in claim 12.

15. The process as claimed in claim 12, wherein the dicarboxylic acid of formula (V) is selected from the group consisting of benzene-1,4-dicarboxylic acid, 2-aminobenzene-1,4-dicarboxylic acid, 2-nitrobenzene-1,4-dicarboxylic acid, 2-chlorobenzene-1,4-dicarboxylic acid, 2-bromobenzene-1,4-dicarboxylic acid, 2,5-dihydroxybenzene-1,4-dicarboxylic acid, 2-methylbenzene-1,4-dicarboxylic acid, 2,5-dimethylbenzene-1,4-dicarboxylic acid, diphenyl-4,4'-dicarboxylic acid, diphenyl-3,3'-dicarboxylic acid, 4,4'-(diazene-1,2-diyl)dibenzoic acid, 3,3'-(diazene-1,2-diyl)dibenzoic acid, naphthalene-2,6-dicarboxylic acid, naphthalene-1,5-dicarboxylic acid, 1,4-phenylenediacetic acid, 1,4-phenylenediacrylic acid and 4,4'-benzophenonedicarboxylic acid.

16. The process as claimed in claim 15, wherein the dicarboxylic acid of formula (V) is selected from the group consisting of benzene-1,4-dicarboxylic acid, 2,5-dihydroxybenzene-1,4-dicarboxylic acid and 2-aminobenzene-1,4-dicarboxylic acid.

17. The process as claimed in claim 11, wherein within the reaction mixture, the titanium alkoxide of formula (III) or titanium oxo complex of formula (IV)/dicarboxylic acid of formula (V) molar ratio varies from 0.1 to 2.

18. The process as claimed in claim 11, wherein the polar solvents used during the fifth step are chosen from mixtures of at least two organic solvents S1 and S2 comprising at least one solvent S1 selected from the group consisting of $C_1$-$C_4$ alcohols, benzyl alcohol and chlorobenzyl alcohol, and at least one solvent S2 selected from the group consisting of N,N-dimethylformamide, N,N-diethylformamide, dimethylsulfoxide, ethylene glycol, dioxane, acetonitrile, acetone, tetrahydrofuran, pyridine and N-methylpyrrolidone.

19. The process as claimed in claim 11, wherein the dicarboxylic acids of formula (VI) are selected from the group consisting of thiophene-2,5-dicarboxylic acid, pyridine-2,6-dicarboxylic acid and pyrazine-2,6-dicarboxylic acid.

20. The process as claimed in claim 11, wherein the solid material resulting from the fourth step/dicarboxylic acid of formula (VI) molar ratio during the fifth step varies from 1 to 20.

\* \* \* \* \*

UNITED STATES PATENT AND TRADEMARK OFFICE
CERTIFICATE OF CORRECTION

PATENT NO. : 8,940,392 B2  
APPLICATION NO. : 13/146720  
DATED : January 27, 2015  
INVENTOR(S) : Serre et al.

Page 1 of 1

It is certified that error appears in the above-identified patent and that said Letters Patent is hereby corrected as shown below:

In the Claims

Column 23, Claim 1, Line 25: Between the words "substituents" and "independently" insert the variable --R--

Column 23, Claim 2, Line 60: "C(sub1)-C(sub1)" should read "C(sub1)-C(sub4)"

Column 23, Claim 2, Line 60: "alkene" between the words "or" and "chains" should read "alkyne"

Column 25, Claim 7, Line 38: "(I-4)" should read "(I-1)"

Column 25, Claim 8, Line 56: "tree" between the words "a" and "diameter" should read "free"

Column 26, Claim 12, Line 27: "Hock" between the words "building" and "constitued" should read "block"

Column 26, Claim 12, Line 54: "ethylene" between "dimethylsulfoxide" and "dioxane" should read "ethylene glycol"

Signed and Sealed this  
Fifteenth Day of September, 2015

Michelle K. Lee  
*Director of the United States Patent and Trademark Office*